United States Patent [19]
Watanabe et al.

[11] Patent Number: 6,008,218
[45] Date of Patent: Dec. 28, 1999

[54] N-PHENYL CARBAMATE COMPOUNDS, PROCESS FOR PRODUCING THE SAME, AND AGRICULTURAL OR HORTICULTURAL BACTERICIDES

[75] Inventors: Masanori Watanabe; Toshinobu Tanaka; Shin Suizu; Tadashi Murakami; Takehiko Asahara, all of Ube, Japan

[73] Assignee: Ube Industries, Ltd., Yamaguchi, Japan

[21] Appl. No.: 09/091,012

[22] PCT Filed: Dec. 6, 1996

[86] PCT No.: PCT/JP96/03597

§ 371 Date: Jun. 8, 1998

§ 102(e) Date: Jun. 8, 1998

[87] PCT Pub. No.: WO97/21689

PCT Pub. Date: Jun. 19, 1997

[30] Foreign Application Priority Data

Dec. 8, 1995 [JP] Japan ................................. 7-320647
Feb. 6, 1996 [JP] Japan ................................. 8-020220

[51] Int. Cl.$^6$ .................... A01N 43/84; C07D 265/36; C07D 279/16
[52] U.S. Cl. ................... 514/224.2; 514/230.5; 544/52; 544/105
[58] Field of Search ............ 544/52, 105; 514/224.2, 514/230.5

[56] References Cited

U.S. PATENT DOCUMENTS 4,337,357 6/1982 Uematsu et al. .................. 564/154

FOREIGN PATENT DOCUMENTS

| | | |
|---|---|---|
| 0085881 | 8/1983 | European Pat. Off. . |
| 0162776 | 11/1985 | European Pat. Off. . |
| 0237781 | 9/1987 | European Pat. Off. . |
| 0170191 | 11/1989 | European Pat. Off. . |
| 0 498 396 | 8/1992 | European Pat. Off. . |
| 0769495 | 4/1997 | European Pat. Off. . |
| 1561854 | 3/1969 | France . |
| 2035749 | 12/1970 | France . |
| 2168140 | 8/1973 | France . |
| 2254333 | 7/1975 | France . |
| 1446622 | 10/1996 | France . |
| 60-126274 | 7/1985 | Japan . |
| 2101068 | 4/1990 | Japan . |
| 9315074 | 8/1993 | WIPO . |

OTHER PUBLICATIONS

Chemical Abstracts, XP002094340, (1991).
Chemical Abstracts, XP002094339, (1992).
Chemical Abstracts, XP002094338, (1989).
Chemical Abstracts, XP002094343, (1957).
Chemical Abstracts, XP002094342, (1966).
Chemical Abstracts, XP002094341, (1969).

*Primary Examiner*—Richard L. Raymond
*Attorney, Agent, or Firm*—Browdy and Neimark

[57] ABSTRACT

This invention relates to An N-phenyl carbamate compound which is represented by the following formula (1):

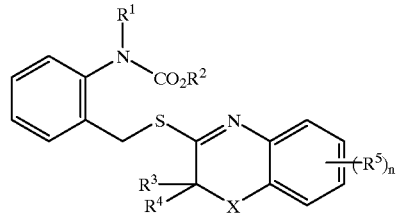

(1)

wherein $R^1$ represents a hydrogen atom, an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ or an alkoxy group having 1 to 4 carbon atoms;

where $R^6$ represents an alkyl group having 1 to 4 carbon atoms;

$R^2$ represents an alkyl group having 1 to 4 carbon atoms;

$R^3$ and $R^4$ each independently represent a hydrogen atom or an alkyl group having 1 to 4 carbon atoms;

$R^5$ represents a hydrogen atom, an alkyl group having 1 to 8 carbon atoms, a haloalkyl group having 1 to 4 carbon atoms, a halogen atom, an alkylcarbonyl group having 2 to 5 carbon atoms, a phenyl group, an alkoxycarbonyl group having 2 to 5 carbon atoms, an alkylsulfonyl group having 1 to 4 carbon atoms, a nitro group, a cyano group, a benzyloxycarbonyl group or a haloalkoxy group having 1 to 4 carbon atoms;

X represents O or S; and n represents 1, 2 or 3;

a process for producing the same and an agricultural or horticultural fungicide containing the compound as an effective ingredient.

14 Claims, No Drawings

N-PHENYL CARBAMATE COMPOUNDS, PROCESS FOR PRODUCING THE SAME, AND AGRICULTURAL OR HORTICULTURAL BACTERICIDES

TECHNICAL FIELD

This invention relates to a novel N-phenyl carbamate compound which is useful as an agricultural or horticultural fungicide.

BACKGROUND ART

As the compound which is similar to the novel N-phenyl carbamate compound of the present invention, the compound represented by the following formula:

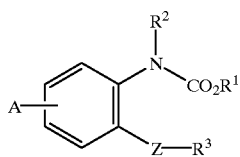

wherein $R^1$ represents an alkyl group; $R^2$ represents a hydrogen atom, an alkyl group, an alkenyl group, an alkynyl group, a CO-(alkyl group), a cycloalkyl group; Z represents $CH_2S$, $CH_2ON=C$-(hydrogen atom, etc.), or the like; $R^3$ represents a benzoxazolyl group, a benzothiazolyl group, etc.; A represents a hydrogen atom, etc. Incidentally, the definitions for $R^1$ to $R^3$, Z and A used in the description of this compound are limited only to the description of this compound, has been described in Japanese Provisional Patent Publication No. 170726/1993.

However, in the above-mentioned publication, there is no exemplary description of the compound having the combination of the substituents which show the N-phenyl carbamate compound of the present invention.

And, in the above-mentioned publication, when an exemplary compound which is similar to the N-phenyl carbamate compound of the present invention is forced to be mentioned, those shown in Table 1 can be mentioned, but physical properties and fungicidal effects thereof have not yet been confirmed.

TABLE 1

Compound No. 362

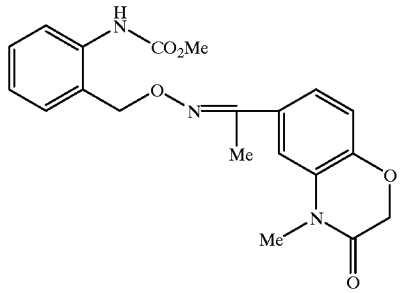

TABLE 1-continued

Compound No. 363

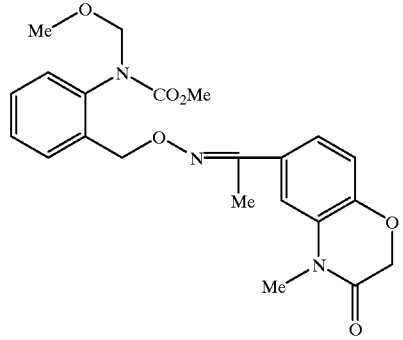

Compound No. 364

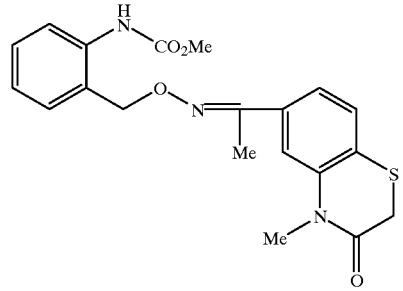

The problem of the present invention is to provide a novel N-phenyl carbamate compound which is useful as an agricultural or horticultural fungicide containing the same as an effective ingredient.

DISCLOSURE OF THE INVENTION

The present inventors have investigated to solve the above problems and as the results, they have found that a novel N-phenyl carbamate compound has an excellent fungicidal effect whereby accomplished the present invention.

That is, the present invention is as follows:

The first invention relates to an N-phenyl carbamate compound (Compound (1)) represented by the following formula (1):

(1)

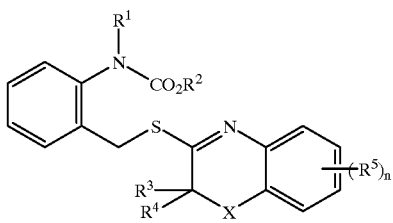

wherein $R^1$ represents a hydrogen atom, an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ (here, $R^6$ represents an alkyl group having 1 to 4 carbon atoms) or an alkoxy group having 1 to 4 carbon atoms;

$R^2$ represents an alkyl group having 1 to 4 carbon atoms;

$R^3$ and $R^4$ each independently represent a hydrogen atom or an alkyl group having 1 to 4 carbon atoms;

$R^5$ represents a hydrogen atom, an alkyl group having 1 to 8 carbon atoms, a haloalkyl group having 1 to 4 carbon atoms, a halogen atom, an alkylcarbonyl group having 2 to 5 carbon atoms, a phenyl group, an alkoxycarbonyl group having 2 to 5 carbon atoms, an alkylsulfonyl group having 1 to 4 carbon atoms, a nitro group, a cyano group, a benzyloxycarbonyl group or a haloalkoxy group having 1 to 4 carbon atoms;

X represents O or S; and n represents 1, 2 or 3.

The second invention relates to a process for producing an N-phenyl carbamate compound (Compound (1-a)) represented by the following formula (1-a) in the above formula (1)

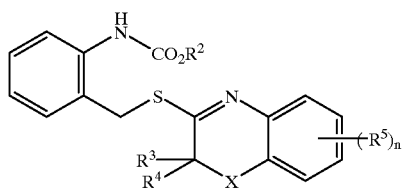

(1-a)

wherein $R^2$ to $R^5$, X and n have the same meanings as defined above, which comprises reacting a compound (Compound (2)) represented by the formula (2):

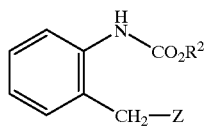

(2)

wherein $R^2$ has the same meaning as defined above; and Z is a chlorine atom or a bromine atom, and a compound (Compound (3)) represented by the following formula (3):

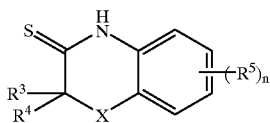

(3)

wherein $R^3$ to $R^5$, X and n have the same meanings as defined above.

The third invention relates to a process for producing an N-phenyl carbamate compound (Compound (1-b)) represented by the following formula (1-b) in the above formula (1)

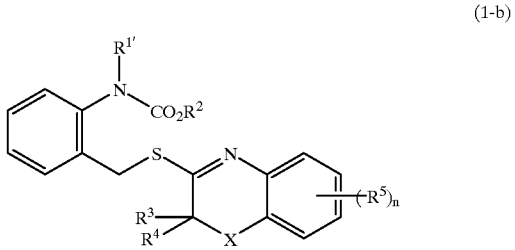

(1-b)

wherein $R^{1'}$ represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms or $CO_2R^6$ (here, $R^6$ represents an alkyl group having 1 to 4 carbon atoms); $R^2$ to $R^5$, X and n have the same meanings as defined above, which comprises reacting the compound (1-a) and a compound (Compound (4)) represented by the formula (4):

$(R^1{-}W)$ or $(R^{1'}{}_2SO_4)$ (4)

wherein $R^{1'}$ has the same meaning as defined above; W represents a chlorine atom, a bromine atom or an iodine atom.

The fourth invention relates to a process for producing an N-phenyl carbamate compound represented by the following formula (1-c) in the above-mentioned formula (1):

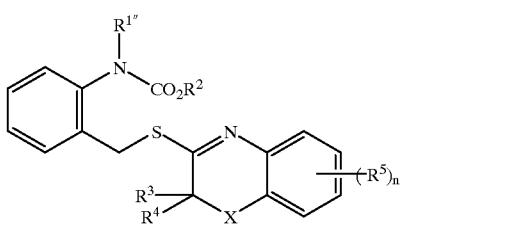

(1-c)

wherein $R^{1''}$ represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ (here, $R^6$ represents an alkyl group having 1 to 4 carbon atoms) or an alkoxy group having 1 to 4 carbon atoms; $R^2$ to $R^5$, X and n have the same meanings as defined above, which comprises reacting a compound represented by the following formula (5):

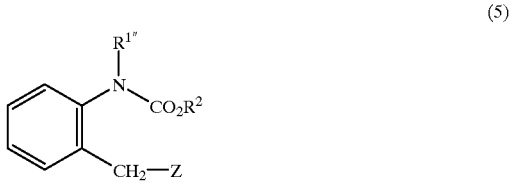

(5)

wherein $R^{1''}$, $R^2$ and Z have the same meanings as defined above, and the compound represented by the above-mentioned formula (3).

The fifth invention relates to a benzoxazine compound represented by the following formula (3'):

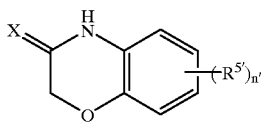

(3')

wherein $R^{5'}$ represents a haloalkoxy group having 1 to 4 carbon atoms, a haloalkyl group having 1 to 4 carbon atoms or a halogen atom; n' represents 1 or 2; and X has the same meaning as defined above.

The sixth invention relates to an agricultural or horticultural fungicide containing Compound (1) as an effective ingredient.

BEST MODE FOR PRACTICING THE INVENTION

In the following, the present invention is explained in detail.

$R^1$ to $R^5$, X, n, Z, W, etc. shown in the novel N-phenyl carbamate compound which is a desired compound and starting materials (Compounds (2) to (5)) for preparation thereof are as follows.

($R^1$)

As $R^1$, there may be mentioned a hydrogen atom, an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ or an alkoxy group having 1 to 4 carbon atoms.

As the alkoxyalkyl group, a straight or branched one may be mentioned, and preferably $CH_2OCH_3$ and $CH_2OC_2H_5$.

As the alkynyl group, a straight or branched one may be mentioned, and preferably $CH_2C\equiv CH$.

As the alkyl group, a straight or branched one may be mentioned, and preferably $CH_3$, $C_2H_5$ and $n-C_3H_7$.

As the alkenyl group, a straight or branched one may be mentioned, and preferably $CH_2CH=CH_2$.

As $R^6$ in $CO_2R^6$, a straight or branched alkyl group having 1 to 4 carbon atoms may be mentioned, and further preferably a methyl group.

As the alkoxy group, a straight or branched one may be mentioned, and preferably $OCH_3$ and $OC_2H_5$.

($R^2$)

As $R^2$, a straight or branched alkyl group having 1 to 4 carbon atoms may be mentioned, and preferably $CH_3$ and $C_2H_5$.

($R^3$ and $R^4$)

As $R^3$ and $R^4$, there may be mentioned each independently a hydrogen atom or an alkyl group having 1 to 4 carbon atoms.

As the alkyl group, a straight or branched one may be mentioned, and preferably $CH_3$ and $C_2H_5$.

(X)

As X, O and S can be mentioned.

($R^5$)

As $R^5$, a hydrogen atom, an alkyl group having 1 to 8 carbon atoms, a haloalkyl group having 1 to 4 carbon atoms, a halogen atom, an alkylcarbonyl group having 2 to 5 carbon atoms, a phenyl group, an alkoxycarbonyl group having 2 to 5 carbon atoms, an alkylsulfonyl group having 1 to 4 carbon atoms, a nitro group, a cyano group, a benzyloxycarbonyl group, a haloalkoxy group having 1 to 4 carbon atoms, etc. may be mentioned.

As the alkyl group, a straight or branched one may be mentioned, and preferably those having 1 to 6 carbon atoms, more preferably $CH_3$, $C_2H_5$, $n-C_3H_7$, $n-C_4H_9$, $t-C_4H_9$, $n-C_5H_{11}$ and $n-C_6H_{13}$.

The substitute position of the alkyl group is not particularly limited; and preferably 5- to 7-position when n is 1 and 6- to 8-position when n is 2.

As the haloalkyl group, a straight or branched one may be mentioned.

As the halogen atom in the haloalkyl group, a chlorine atom, an iodine atom, a bromine atom, a fluorine atom, etc. may be mentioned, and preferably a fluorine atom.

As the alkyl group in the haloalkyl group, a straight or branched one may be mentioned, and preferably a methyl group.

The most preferred one as the haloalkyl group is a trifluoromethyl group.

The substitute position of the haloalkyl group is not particularly limited; and preferably 6- or 8-position when n is 1.

As the halogen atom, a chlorine atom, an iodine atom, a bromine atom, a fluorine atom, etc. may be mentioned, and preferably a fluorine atom.

The substitute position of the halogen atom is not particularly limited, and preferably 6-position when n is 1, 5- to 8-position when n is 2 and 5-, 6- and 8-position when n is 3.

As the alkylcarbonyl group, a straight or branched one may be mentioned, and the alkyl group thereof is preferably an ethyl group.

The substitute position of the alkylcarbonyl group is not particularly limited, and preferably 6-position when n is 1.

The substitute position of the phenyl group is not particularly limited, and preferably 6-position when n is 1.

As the alkoxycarbonyl group, a straight or branched one may be mentioned, and the alkyl group thereof is preferably a methyl group and a propyl group.

The substitute position of the alkoxycarbonyl group is not particularly limited, and preferably 6-position when n is 1.

As the alkylsulfonyl group, a straight or branched one may be mentioned, and the alkyl group thereof is preferably an ethyl group.

The substitute position of the alkylsulfonyl group is not particularly limited, and preferably 6-position when n is 1.

The substitute position of the nitro group is not particularly limited, and preferably 5- to 7-position.

The substitute position of the cyano group is not particularly limited, and preferably 6- to 8-position, more preferably 6-position and 8-position.

As the haloalkoxy group, a straight or branched one may be mentioned, and preferably a trifluoromethoxy group.

The substitute position of the haloalkoxy group is not particularly limited, and preferably 6-position.

The substitute position of the benzyloxycarbonyl group is not particularly limited, and preferably 6-position.

($R^{5'}$)

As $R^{5'}$, a haloalkoxy group having 1 to 4 carbon atoms, a haloalkyl group having 1 to 4 carbon atoms, a halogen atom or a halogen atom may be mentioned.

As the haloalkoxy group, a straight or branched one may be mentioned.

As the haloalkoxy group, a straight or branched one may be mentioned.

As the halogen atom in the haloalkoxy group, a chlorine atom, an iodine atom, a bromine atom, a fluorine atom, etc. may be mentioned, and preferably a fluorine atom.

As the alkoxy group in the haloalkoxy group, a straight or branched one may be mentioned, and preferably a methoxy group.

The most preferred one as the haloalkoxy group is a trifluoromethoxy group.

The substitute position of the haloalkoxy group is not particularly limited, and preferably 6-position.

As the haloalkyl group, a straight or branched one may be mentioned.

As the halogen atom in the haloalkyl group, a chlorine atom, an iodine atom, a bromine atom, a fluorine atom, etc. may be mentioned, and preferably a fluorine atom.

As the alkyl group in the haloalkyl group, a straight or branched one may be mentioned, and preferably a methyl group.

The most preferred one as the haloalkyl group is a trifluoromethyl group.

The substitute position of the haloalkyl group is not particularly limited; and preferably 5- or 7-position.

As the halogen atom, a chlorine atom, an iodine atom, a bromine atom, a fluorine atom, etc. may be mentioned, and preferably a chlorine atom and a fluorine atom.

The substitute position of the halogen atom is not particularly limited, and preferably 6- or 8-position.

n is 1, 2 and 3, and preferably 1 and 2.

n' is 1 and 2.

As the compound (1), there may be mentioned compounds comprising a combination of various substituents described above. From the point of fungicidal effects, the following compounds are preferred.

(1) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and $(R^5)_n$ is a hydrogen atom.

(2) A compound in which $R^1$ is an alkoxyalkyl group having 2 to 5 carbon atoms, $R^1$ is an alkyl group having 1 to 4 carbon atoms, $R^3$ and $R^4$ are both hydrogen atoms, X is a sulfur atom, and $(R^5)_n$ is a hydrogen atom.

(3) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkyl group having 1 to 4 carbon atoms (preferably the substitution position is 5-, 6- or 7-position).

(4) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_5$ is 1 and $R^5$ is a haloalkyl group having 1 to 4 carbon atoms (preferably the substitution position is 6- or 8-position).

(5) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a haloalkyl group having 1 to 4 carbon atoms (preferably the substitution position is 6- or 8-position).

(6) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a halogen atom (preferably the substitution position is 6-position).

(7) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a halogen atom (preferably the substitution position is 6-position).

(8) A compound in which $R^1$ is an alkoxyalkyl group having 2 to 5 carbon atoms, $R^2$ and $R^3$ are alkyl groups having 1 to 4 carbon atoms, $R^4$ is a hydrogen atom, X is an oxygen atom, and n in $(R^5)_n$ is 1 and $R^5$ is a halogen atom (preferably the substitution position is 6-position).

(9) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkyl group having 1 to 4 carbon atoms (preferably the substitution position is 5-, 6- or 7-position).

(10) A compound in which $R^1$, $R^3$ and $R^4$ are all hydrogen atoms, $R^2$ is an alkyl group having 1 to 4 carbon atoms, X is an oxygen atom, and n in $(R^5)_n$ is 2 and $R^5$ are an alkyl group having 1 to 4 carbon atoms (preferably the substitution position is 6-, 7- or 8-position) and a halogen atom (preferably the substitution position is 6- or 8-position).

(11) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are an alkyl group having 1 to 4 carbon atoms (preferably the substitution position is 6-, 7- or 8-position) and a halogen atom (preferably the substitution position is 6- or 8-position).

(12) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are an alkyl group having 1 to 4 carbon atoms (preferably the substitution position is 6-, 7- or 8-position) and a halogen atom (preferably the substitution position is 6- or 8-position).

(13) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are a haloalkyl group having 1 to 4 carbon atoms (preferably the substitution position is 6-position) and a halogen atom (preferably the substitution position is 8-position).

(14) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are a haloalkyl group having 1 to 4 carbon atoms (preferably the substitution position is 6-position) and a halogen atom (preferably the substitution position is 8-position).

(15) A compound in which $R^1$, $R^3$ and $R^4$ are all hydrogen atoms, $R^2$ is an alkyl group having 1 to 4 carbon atoms, X is an oxygen atom, and n in $(R^5)_n$ is 2 and $R^5$'s are halogen atoms (preferably the substitution positions are 6-, 7- or 8-position).

(16) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are halogen atoms (preferably the substitution positions are 6-, 7- or 8-position).

(17) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are halogen atoms (preferably the substitution positions are 6-, 7- or 8-position).

(18) A compound in which $R^1$ and $R^2$ are both alkyl groups having 1 to 4 carbon atoms, $R^3$ and $R^4$ are both hydrogen atoms, X is an oxygen atom, and n in $(R^5)_n$ is 2 and $R^5$'s are an alkyl group having 1 to 4 carbon atoms (preferably the substitution position is 6-, 7- or 8-position) and a halogen atom (preferably the substitution position is 6- or 8-position).

(19) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkyl group having 1 to 4 carbon atoms (preferably the substitution position is 5-, 6- or 7-position).

(20) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a haloalkyl group having 1 to 4 carbon atoms (preferably the substitution position is 6- or 8-position).

(21) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a halogen atom (preferably the substitution position is 6-position).

(22) A compound in which $R^1$ is an alkoxy group having 1 to 4 carbon atoms, $R^2$ is an alkyl group having 1 to 4 carbon atoms, $R^3$ is an alkyl group having 1 to 4 carbon atoms, $R^4$ is a hydrogen atom, X is an oxygen atom, and n in $(R^5)_n$ is 1 and $R^5$ is a halogen atom (preferably the substitution position is 6-position).

(23) A compound in which $R^1$ is an alkoxy group having 1 to 4 carbon atoms, $R^2$ to $R^4$ are alkyl groups having 1 to 4 carbon atoms, X is an oxygen atom, and n in $(R^5)_n$ is 1 and $R^5$ is a halogen atom (preferably the substitution position is 8- position).

(24) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are halogen atom (preferably the substitution position is 5- or 8-position) and $NO_2$ (preferably the substitution position is 7-position).

(25) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are an alkyl group having 1 to 4 carbon atoms (preferably the substitution position is 6-, 7- or 8-position) and a halogen atom (preferably the substitution position is 6- or 8-position).

(26) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are a haloalkyl group having 1 to 4 carbon atoms (preferably the substitution position is 6-position) and a halogen atom (preferably the substitution position is 8-position).

(27) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is a phenyl group.

(28) A compound in which $R^1$ is an alkoxy group having 1 to 4 carbon atoms, $R^2$ and $R^3$ are both alkyl groups having 1 to 4 carbon atoms, $R^4$ is a hydrogen atom, X is an oxygen atom, and n in $(R^5)_n$ is 1 and $R^5$ is an alkylcarbonyl group having 2 to 5 carbon atoms.

(29) A compound in which $R^1$ is an alkoxy group having 1 to 4 carbon atoms, $R^2$ to $R^4$ are alkyl groups each having 1 to 4 carbon atoms, X is an oxygen atom, and n in $(R^5)_n$ is 2 and $R^5$'s are a haloalkyl group having 1 to 4 carbon atoms (preferably the substitution position is 6-position) and a halogen atom (preferable the substitution position is 8-position).

(30) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkylsulfonyl group having 1 to 4 carbon atoms.

(31) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkoxycarbonyl group having 2 to 5 carbon atoms.

(32) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are a haloalkoxy group having 1 to 4 carbon atoms (preferably the substitution position is 6-position) and a halogen atom (preferably the substitution position is 8-position).

(33) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are a haloalkoxy group having 1 to 4 carbon atoms (preferably the substitution position is 6-position) and a halogen atom (preferably the substitution position is 8-position).

(34) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, and n in $(R^5)_n$ is 1 and $R^5$ is an alkyl group having 1 to 8 carbon atoms (preferably the substitution position is 5-, 6- or 7-position).

(35) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, and n in $(R^5)_n$ is 2 and $R^5$'s are an alkylcarbonyl group having 2 to 5 carbon atoms (preferably the substitution position is 6- or 8-position) and a halogen atom (preferably the substitution position is 5-, 6- or 7-positoin).

(36) A compound in which $R^1$ and $R^2$ are both alkyl groups having 1 to 4 carbon atoms, $R^3$ and $R^4$ are both hydrogen atoms, X is an oxygen atom, and n in $(R^5)_n$ is 1 and $R^5$ is a halogen atom (preferably the substitution position is 6- or 8-position).

As to $R^1$ to $R^5$, X and n, those which are mentioned as preferred ones, and further preferred ones may be mentioned in the above-identified explanations.

Specific compounds (1) thereof may be mentioned Compounds Nos. 2, 8, 10, 17, 20, 23, 25, 27, 30, 33, 38, 45, 46, 54, 60 to 62, 64, 66, 68 to 70, 72, 74, 75, 82, 86, 87, 89~91, 96, 98, 99, 101 to 105, 108, 109, 111, 113~124, 126, 127, 135, 141 and 144 may be mentioned as described in Tables 3 and 4 mentioned herein below.

Compound (1) can be synthesized by the Synthetic methods 1 to 3 shown below.

(Synthetic method 1)

The compound (1-a) (a compound in which $R^1$ in Compound (1) is a hydrogen atom) can be prepared by reacting Compound (2) and Compound (3) in a solvent as shown below. This reaction can be promoted in the presence of a base.

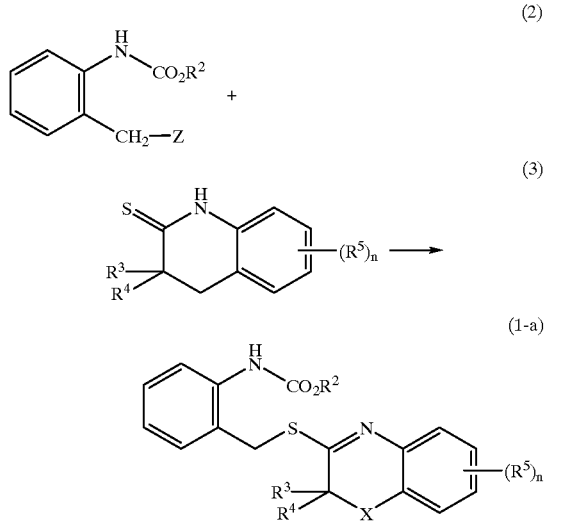

Wherein $R^2$ to $R^5$, Z, X and n have the same meanings as defined above.

As the kind of the solvent, it is not particularly limited so long as it does not directly participate the present invention, and there may be mentioned, for example, an alcohol such as isopropanol, t-butanol, diethyleneglycol, etc.; a ketone such as acetone, methyl ethyl ketone, cyclohexanone, etc.; an aliphatic hydrocarbons such as n-hexane, cyclohexane, etc.; an ether such as diethyl ether, diisopropyl ether, tetrahydrofuran, dioxane, etc.; a halogenated hydrocarbon such as dichloroethane, carbon tetrachloride, tetrachloroethane, etc.; an aromatic hydrocarbon such as benzene, chlorobenzene, nitrobenzene, toluene, xylene, etc.; a nitrile such as acetonitrile, propionitrile, etc.; a polar solvent such as dimethylformamide, dimethylsulfoxide, sulforane, etc.; a mixture thereof and the like.

An amount of the solvent to be used can be used so that Compound (2) becomes 0.1 to 80% by weight; and preferably 0.1 to 40% by weight.

As a base, an inorganic base and an organic base may be used, and preferably an organic base.

As the inorganic base, there may be mentioned, for example, a carbonate (or a hydroxide) of an alkali metal or an alkaline earth metal such as sodium carbonate, potassium carbonate, calcium carbonate, sodium hydrogen carbonate, sodium hydroxide, potassium hydroxide, calcium hydroxide, etc., and a hydride of an alkali metal such as lithium hydride, sodium hydride, etc.

As the organic base, there may be mentioned an alkali metal alkoxide such as sodium methoxide, potassium t-butoxide, diethylamine, triethylamine, pyridine, etc.

An amount of the base is generally 0.001 to 5-fold moles, and preferably 0.8 to 2-fold moles based on Compound (2).

The reaction temperature is within the temperature range of from −40° C. to not more than the boiling point of the solvent to be used, and preferably 0 to 70° C.

The reaction time may vary depending on the concentration and the temperature mentioned above, it is generally 0.5 to 24 hours, and preferably 1 to 10 hours.

Compound (2) can be synthesized according to the method described in Japanese Provisional Patent Publication No. 170726/1993.

Compound (3) can be obtained in accordance with the method described in Japanese Provisional Patent Publication No. 145678/1979 (which corresponds to U.S. Pat. No. 4,268,301 and No. 4,337,357) as mentioned below by selectively nitrating the ortho position of the corresponding substituted phenol and reducing the same to prepare a 2-amino(thio)phenol derivative, then reacting the resulting material with $Y^1CR^3R^4COY^2$ ($R^3$ and $R^4$ have the same meanings as defined above. $Y^1$ and $Y^2$ each independently represent a chlorine atom, a bromine atom or an iodine atom.) in the presence of a base to make a benzoxazine compound or a benzothiazine compound, and then reacting a sulfurizing reagent (phosphorus pentasulfide, Lawesson's reagent, etc.) thereto.

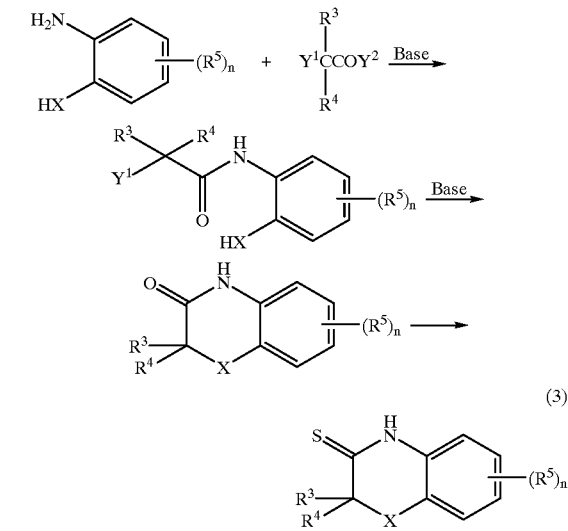

wherein $R^3$ to $R^5$, X, n, $Y^1$ and $Y^2$ have the same meanings as defined above.

Among Compound (3) thus obtained, novel compounds (Compound (3')) such as Compound (3'-1) to Compound (3'-8), etc. are shown in Table 2 mentioned hereinbelow.

The desired compound (1-a) shown in Table 3 mentioned hereinbelow prepared as described above is subjected to the usual post-treatment such as extraction, concentration, filtration, etc. after completion of the reaction, and optionally purified by the well-known means such as recrystallization, various kinds of chromatography, etc., if necessary.

(Synthetic method 2)

The compound (1-b) (a compound in which $R^1$ in Compound (1) is an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms or $CO_2R^6$ (where $R^6$ represents an alkyl group having 1 to 4 carbon atoms)) can be prepared by reacting Compound (1-a) and Compound (4) in a solvent as shown below. This reaction can be promoted in the presence of a base. Also, depending on necessity, a catalyst may be used.

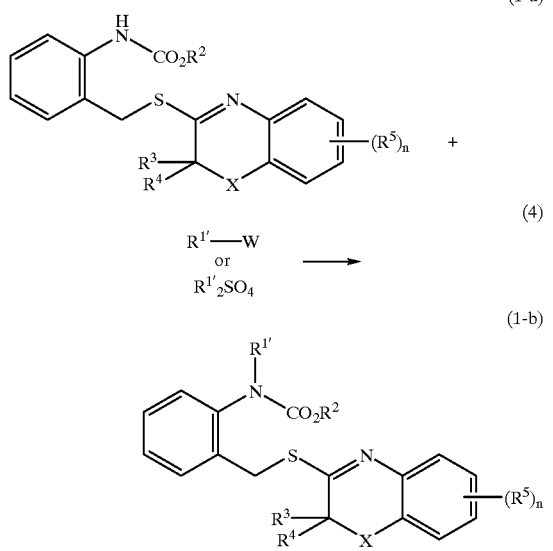

wherein $R^2$ to $R^5$, X, n, $R^{1'}$ and W have the same meanings as defined above.

As the kind of the solvent, it is not particularly limited so long as it does not participate the present reaction, and for example, those mentioned in Synthetic example 1 may be mentioned.

An amount of the solvent to be used may be generally such an amount that Compound (1-a) becomes 0.1 to 80% by weight; preferably 0.1 to 40% by weight.

As the base, those as mentioned in Synthetic method 1 may be mentioned, and preferably an inorganic base.

An amount of the base to be used is generally 0.001 to 5-fold moles based on Compound (1-a), but preferably 0.8 to 2-fold moles.

The reaction temperature is within the temperature range of −40° C. to the boiling point of the used solvent or less, preferably −10 to 70° C.

As the catalyst, there may be mentioned benzyl triethyl ammonium chloride, tetrabutyl ammonium bromide, etc.

An amount of the catalyst to be used is generally 1 to 20% by weight based on the weight of Compound (1-a), preferably 3 to 10% by weight.

The reaction time may vary depending on the concentration and the temperature mentioned above, but usually an instant to 12 hours, preferably 0.5 to 8 hours.

As Compound (4), a commercially available product can be used.

The desired Compound (1-b) shown in Table 3 mentioned hereinbelow prepared as mentioned above is subjected to the usual post-treatment such as extraction, concentration, filtration, etc. after completion of the reaction, and optionally purified by the well-known means such as recrystallization, various kinds of chromatography, etc., if necessary.

(Synthetic method 3)

Compound (1-C) can be produced by reacting Compound (3) and Compound (5) in a solvent as shown below. This reaction can be promoted in the presence of a base.

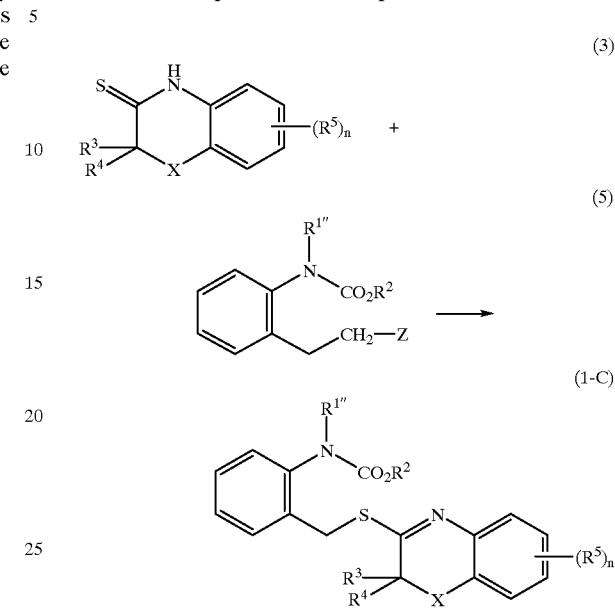

wherein $R^{1''}$, $R^2$ to $R^5$, X, and n have the same meanings as defined above.

As the kind of the solvent, it is not particularly limited so long as it does not participate the present reaction, and for example, those mentioned in Synthetic example 1 may be mentioned.

An amount of the solvent to be used may be generally such an amount that Compound (5) becomes 0.1 to 80% by weight; preferably 0.1 to 40% by weight.

As the base, those as mentioned in Synthetic method 1 may be mentioned, and preferably an organic base.

An amount of the base to be used is generally 0.001 to 5-fold moles based on Compound (5), but preferably 0.8 to 2-fold moles.

The reaction temperature is within the temperature range of −40° C. to the boiling point of the used solvent or less, preferably 0 to 70° C.

The reaction time may vary depending on the concentration and the temperature mentioned above, but usually 0.5 to 24 hours, preferably 1 to 10 hours.

Compound (5) can be synthesized as shown below by reacting 2-aminobenzyl alcohol and Compound (4), and further reacting $ClCO_2R^2$ (where $R^2$ has the same meaning as defined above) in the presence of a base, then subjecting to usual chlorination reaction by the use of $SOCl_2$ in neutral or basic conditions, or subjecting to usual bromination reaction by the use of $SOBr_2$.

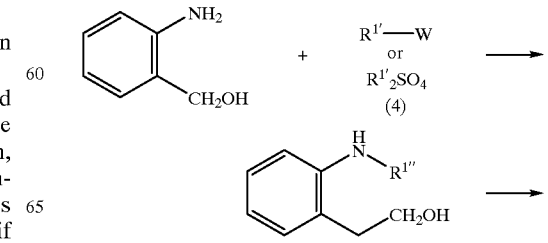

-continued

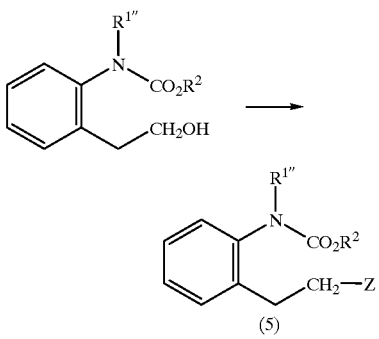

wherein $R^{1''}$, W, $R^2$ and Z have the same meanings as defined above.

When $R^1$ in Compound (5) is an alkoxy group having 1 to 4 carbon atoms, it can be synthesized, for example, as shown below, by reducing 2-nitrotoluene according to the method described in Japanese Provisional Patent Publication No. 340607/1994 to prepare N-(2-tolyl)hydroxylamine, reacting thereto $ClCO_2R^2$ (where $R^2$ has the same meaning as defined above) in the presence of a base, then subjecting the resulting compound to O-alkylation by using a halogenated alkyl, etc., and further subjecting to the usual chlorination reaction by using NCS (N-chlorosuccinimide) or the usual bromination reaction by using NBS (N-bromosuccinimide).

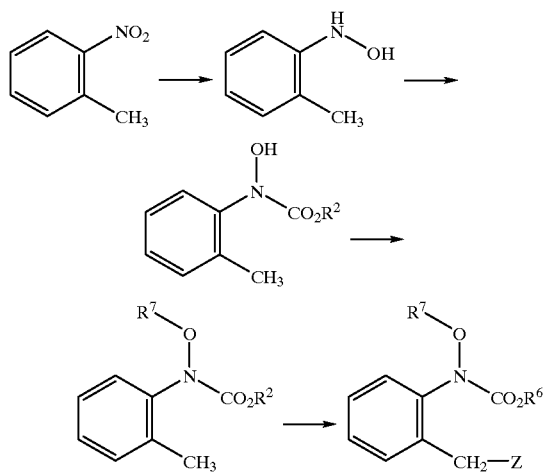

wherein $R^2$, $R^7$ and Z have the same meanings as defined above.

The desired compound (1-b) shown in Table 3 mentioned hereinbelow prepared as mentioned above is subjected to the usual post-treatment such as extraction, concentration, filtration, etc. after completion of the reaction, and optionally purified by the well-known means such as recrystallization, various kinds of chromatography, etc., if necessary.

(Controlling effect of diseases)

As agricultural and horticultural diseases on which a controlling effect by Compound (1) of the present invention can be observed, there may be mentioned, for example, cucumber downy mildew, cucumber gray mold, rice blast, barley powdery mildew, cucumber powdery mildew, wheat brown rust, rice sheath blight, etc.

(Agricultural and horticultural fungicide)

The agricultural and horticultural fungicide of the present invention contains one kind or more of Compound (1) as an effective ingredient.

Compound (1) may be used singly, but usually, it is preferred to formulate a carrier, surfactant, dispersant, auxiliary, etc. (for example, it is prepared as a composition such as dust powder, an emulsifiable concentrate, a fine granule, a granule, a wettable powder, an oily suspension, an aerosol, etc.) according to the conventionally known method.

As the carrier, there may be mentioned, for example, a solid carrier such as bentonite, clay, kaolin, diatomaceous earth, white carbon, vermiculite, calcium hydroxide, siliceous sand, ammonium sulfate, urea, etc., a liquid carrier such as hydrocarbon (kerosine, mineral oil, etc.), aromatic hydrocarbon, (benzene, toluene, xylene, etc.), chlorinated hydrocarbon (chloroform, carbon tetrachloride, etc.), ethers (dioxane, tetrahydrofuran, etc.), ketones (acetone, cyclohexanone, isophorone, etc.), esters (ethyl acetate, ethyleneglycol acetate, dibutyl maleate, etc.), alcohols (methanol, n-hexanone, ethylene glycol, etc.), polar solvent (dimethylformamide, dimethylsulfoxide, etc.), water, etc.; a gas carrier such as air, nitrogen, a carbonic acid gas, fleone, etc. (in this case, mixture spreading can be carried out), and the like.

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

In the following, the present invention is explained by referring to Examples more specifically. These Examples are not intended to limit the scope of the present invention.

Reference example (Synthesis of Compound (3))

(1) 8-Chloro-6-trifluoromethoxy-1,4-benzoxazin-3(4H)-one (Synthesis of Compound (3'-4))

In an Erlenmeyer flask (100 ml volume) was charged 0.64 g (0.016 mole) of sodium hydroxide and it was dissolved in water (3 ml).

To the solution was added 3.0 g (0.013 mole) of 2-amino-6-chloro-4-trifluoromethoxy phenol dissolved in dichloromethane (50 ml), and under ice-cooling, 1.5 g (0.013 mole) of chloroacetyl chloride dissolved in dichloromethane (10 ml) was added dropwise over 5 minutes.

Under ice-cooling, the mixture was stirred for 30 minutes, and then stirred at room temperature for 2 hours. Thereafter, water (30 ml) was added to the reaction mixture, the mixture was stirred for 5 minutes and the dichloromethane phase was separated by a separating funnel.

The dichloromethane layer was then washed with water (50 ml) twice and dried over sodium sulfate.

After filtrating the layer through a cotton stopper, the solvent was removed by distillation and the obtained residue was purified by silica gel column chromatography (Wako gel C-200, eluted by toluene:ehtyl acetate=(50:1) to (4:1)) to obtain 2.5 g (0.0082 mole) of a colorless plate shaped 2-chloro-(3'-chloro-2'-hydroxy-5'-trifluoromethoxy) acetanilide crystal.

2.5 g (0.0082 mole) of this crystal was dissolved in acetone (30 ml), 1.4 g (0.010 mole) of potassium carbonate was added to the mixture, and the mixture was stirred in a 60° C. water bath for 6 hours by attaching a cooling tube.

After completion of the reaction was confirmed by TLC, the reaction mixture was filtered through a cotton stopper and acetone was removed by distillation.

The remaining solid was dissolved in ethyl acetate (50 ml) and washed with water (50 ml) twice.

The ethyl acetate layer was dried over anhydrous sodium sulfate for one hour, then filtered and the solvent was removed by distillation to obtain 1.5 g (0.0056 mole) of the desired compound as pale brownish powder.

(2) 8-Chloro-6-trifluoromethoxy-1,4-benzoxazin-3(4H)-thione (Synthesis of Compound (3'-8))

In toluene (70 ml) was dissolved 1.5 g (0.0056 mole) of 8-chloro-6-trifluoromethoxy-1,4-benzoxazin-3(4H)-one under heating, then 1.1 g (0.028 mole) of Lawesson's reagent and the mixture was further refluxed under heating for 2 hours.

After confirming that the desired compound was formed and the starting materials becomes trace or so by TLC, toluene was removed by distillation.

The obtained residue was purified by silica gel column chromatography (Wako gel C-200, eluted by toluene) to obtain 1.58 g (0.0056 mole) of the desired compound as pale yellowish powder.

(3) Synthesis of other Compound (3) in Table 3

According to the methods described in the above-mentioned (1) and (2), other Compound (3) than the above in Table 3 was synthesized.

Among Compounds (3) thus obtained, novel compounds (Compound (3')) such as Compound (3'-1) to Compound (3'-8) are shown in Table 2 below.

TABLE 2

(3')

| Compound | X | $(R^{5'})_{n'}$ | Physical properties |
|---|---|---|---|
| 3'-1 | O | 6-OCF$_3$ | $^1$H-NMR (25° C., 270 MHz, DMSO-d$_6$): 4.62 (s, 2H), 6.86 (s, 1H), 6.90 (d, 1H, J=8.8 Hz), 7.05 (d, 2H, J=8.8 Hz), 10.6~11.10 (brs, 1H) ppm |
| 3'-2 | O | 5-CF$_3$<br>6-F | m.p.: 86.6~87.3° C.<br>$^1$H-NMR (25° C., 270 MHz, DMSO-d$_6$): 4.62 (s, 2H), 7.06 (dd, 1H, JH=9.5, JF=11.0 Hz), 7.35 (dd, 1H, JH=9.5, JF=5.1 Hz), 10.41 (s, 1H) ppm |
| 3'-3 | O | 6-F<br>7-CF$_3$ | m.p.: 195~197° C.<br>$^1$H-NMR (25° C., 270 MHz, DMSO-d$_6$): 4.67 (s, 2H), 6.89 (d, 1H, JF=11.0 Hz), 7.30 (d, 1H, JF=6.6 Hz), 11.15 (s, 1H) ppm |
| 3'-4 | O | 6-OCF$_3$<br>8-Cl | $^1$H-NMR (25°, 270 MHz, DMSO-d$_6$): 4.75 (s, 2H), 6.68 (d, 1H, J=2.2 Hz), 6.98 (d, 1H, J=2.2 Hz), 9.42 (s, 1H) ppm |
| 3'-5 | S | 6-OCF$_3$ | $^1$H-NMR (27° C., 400 MHz, CDCl$_3$): 4.89 (s, 2H), 6.77 (d, 1H, J=2.9 Hz), 6.89~6.94 (m, 1H), 7.01 (d, 1H, J=8.8 Hz), 9.40~9.58 (brs, 1H) ppm |
| 3'-6 | S | 5-CF$_3$<br>6-F | $^1$H-NMR (27° C., 400 MHz, CDCl$_3$): 4.85 (s, 2H), 6.89 (dd, 1H, JH=8.8, JF=9.8 Hz), 7.18 (dd, 1H, JH=8.8, JF=4.4 Hz), 9.44~9.71 (brs, 1H) ppm |
| 3'-7 | S | 6-F<br>7-CF$_3$ | $^1$H-NMR (27° C., 400 MHz, CDCl$_3$): 4.89 (s, 2H), 6.74 (d, 1H, J=9.8 Hz), 7.23 (d, 1H, J=6.3 Hz), 9.43~9.65 (brs, 1H) ppm |
| 3'-8 | S | 6-OCF$_3$<br>8-Cl | $^1$H-NMR (27° C., 400 MHz, CDCl$_3$): 4.98 (s, 2H), 6.72 (dd, 1H, JH=2.4 Hz, JF=1.0 Hz), 7.04 (dd, 1H, JH=2.4, JF=1.0 Hz), 9.65~9.86 (brs, 1H) ppm |

Example 1 (Synthesis of Compound (1))

(1) Synthesis of methyl N-[2-[(6-trifluoromethyl-2H-1,4-benzoxazin-3-ylthio)methyl]phenyl]carbamate (Compound 22)

Potassium t-butoxide (1.7 g) was added to 6-trifluoromethyl-2-H-1,4-benzoxazin-3-thione (3.0 g) dissolved in tetrahydrofuran (20 ml), and after adding methyl N-[2-(chloromethyl)phenyl]carbamate (2.8 g) dissolved in tetrahydrofuran (10 ml) dropwise at room temperature, the mixture was stirred at room temperature for one hour.

After completion of the reaction, the reaction mixture was poured into water (20 ml) and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 3.7 g of the desired compound as pale yellowish powder-like crystal.

(2) Synthesis of methyl N-(methoxymethyl)-N-[2-[(6-trifluoromethyl-2H-1,4-benzoxazin-3-ylthio)methyl]-phenyl]carbamate (Compound 23)

The compound 22 (1.7 g) obtained in the above-mentioned (1) was dissolved in tetrahydrofuran (15 ml), and potassium hydroxide powder (85%) (0.55 g) and benzyltriethyl ammonium chloride (0.2 g) were added thereto.

To the mixture was added chloromethyl methyl ether (0.6 g) at room temperature and the mixture was stirred at room temperature for one hour.

After completion of the reaction, the reaction mixture was poured into water (20 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 1.5 g of the desired compound as a colorless viscous oily product.

(3) Synthesis of methyl N-(propargyl)-N-[2-[(6-trifluoromethyl-2H-1,4-benzoxazin-3-ylthio)methyl] phenyl]-carbamate (Compound 25)

Potassium t-butoxide (0.2 g) was added to 6-trifluoromethyl-2H-1,4-benzoxazin-3-thione (0.3 g) dissolved in tetrahydrofuran (10 ml), and after adding methyl N-[2-(chloromethyl)phenyl]-N-propargyl carbamate (0.5 g) dissolved in tetrahydrofuran (2 ml) dropwise at room temperature, the mixture was stirred at room temperature for 3 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.3 g of the desired compound as a yellowish viscous oily product.

(4) Synthesis of methyl N-(propargyl)-N-[2-[(6-chloro-2H-1,4-benzoxazin-3-ylthio)methyl]phenyl]carbamate (Compound 33)

Potassium t-butoxide (0.2 g) was added to 6-chloro-2H-1,4-benzoxazin-3-thione (0.3 g) dissolved in tetrahydrofuran (10 ml), and after adding methyl N-[2-(chloromethyl) phenyl]-N-propargyl carbamate (0.5 g) dissolved in tetrahydrofuran (2 ml) dropwise at room temperature, the mixture was stirred at room temperature for 3 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.4 g of the desired compound as a yellowish viscous oily product.

(5) Synthesis of methyl N-[2-[(8-chloro-6-trifluoromethyl-2H-1,4-benzoxazin-3-ylthio)methyl] phenyl]carbamate (Compound 67)

Potassium t-butoxide (0.41 g) was added to 8-chloro-6-trifluoromethyl-2H-1,4-benzoxazin-3-thione (0.85 g) dissolved in tetrahydrofuran (15 ml), and after adding methyl N-[2-(chloromethyl)phenyl]carbamate (0.64 g) dissolved in tetrahydrofuran (5 ml) dropwise at room temperature, the mixture was stirred at room temperature for 2 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 1.1 g of the desired compound as a yellowish powder-like crystal.

(6) Synthesis of methyl N-(methoxymethyl)-N-[2-[(8-chloro-6-trifluoromethyl-2H-1,4-benzoxazin-3-ylthio) methyl]-phenyl]carbamate (Compound 68)

The compound 68 (1.05 g) obtained in the above-mentioned (5) was dissolved in tetrahydrofuran (15 ml), and potassium hydroxide powder (85%) (0.32 g) and benzyltriethyl ammonium chloride (0.1 g) were added thereto.

To the mixture was added chloromethyl methyl ether (0.39 g) at room temperature and the mixture was stirred at room temperature for one hour.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.5 g of the desired compound as pale yellowish powder-like crystal.

(7) Synthesis of methyl N-(propargyl)-N-[2-[(8-chloro-6-trifluoromethyl-2H-1,4-benzoxazin-3-ylthio)methyl]-phenyl]carbamate (Compound 69)

Potassium t-butoxide (0.2 g) was added to 6-trifluoromethyl-2H-1,4-benzoxazin-3-thione (0.3 g) dissolved in tetrahydrofuran (10 ml), and after adding methyl N-[2-(chloromethyl)phenyl]-N-propargyl carbamate (0.4 g) dissolved in tetrahydrofuran (2 ml) dropwise at room temperature, the mixture was stirred at room temperature for 3 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 1.8 g of the desired compound as pale yellowish powder-like crystal.

(8) Synthesis of methyl N-[2-[(6,8-dichloro-2H-1,4-benzoxazin-3-ylthio)methyl]phenyl]carbamate (Compound 73)

Potassium t-butoxide (0.66 g) was added to 6,8-dichloromethyl-2H-1,4-benzoxazin-3-thione (0.3 g) dissolved in tetrahydrofuran (10 ml), and after adding methyl N-[2-(chloromethyl)phenyl]carbamate (1.2 g) dissolved in tetrahydrofuran (5 ml) dropwise at room temperature, the mixture was stirred at room temperature for 2 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 1.8 g of the desired compound as pale yellowish powder-like crystal.

(9) Synthesis of methyl N-(methoxymethyl)-N-[2-[(6,8-dichloro-2H-1,4-benzoxazin-3-ylthio)methyl]phenyl]-carbamate (Compound 74)

The compound 75 (0.7 g) obtained in the above-mentioned (8) was dissolved in tetrahydrofuran (15 ml), and potassium hydroxide powder (85%) (0.32 g) and benzyltriethyl ammonium chloride (0.1 g) were added thereto.

To the mixture was added chloromethyl methyl ether (0.39 g) at room temperature and the mixture was stirred at room temperature for one hour.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.4 g of the desired compound as pale yellowish powder-like crystal.

(10) Synthesis of methyl N-(propargyl)-N-[2-[(6,8-dichloro-2H-1,4-benzoxazin-3-ylthio)methyl]phenyl] carbamate (Compound 75)

Potassium t-butoxide (0.2 g) was added to 6,8-dichloro-2H-1,4-benzoxazin-3-thione (0.3 g) dissolved in tetrahydrofuran (10 ml), and after adding methyl N-[2-(chloromethyl) phenyl]-N-propargyl carbamate (0.4 g) dissolved in tetrahydrofuran (2 ml) dropwise at room temperature, the mixture was stirred at room temperature for 4 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.3 g of the desired compound as pale yellowish powder-like crystal.

(11) Synthesis of methyl N-[2-[(6-chloro-2H-1,4-benzoxazin-3-ylthio)methyl]phenyl]-N-methoxycarbamate (Compound 89)

Potassium t-butoxide (0.25 g) was added to 6-chloro-2H-1,4-benzoxazin-3-thione (0.5 g) dissolved in tetrahydrofuran (10 ml), and after adding methyl N-[2-(bromomethyl)phenyl]-N-methoxy carbamate (0.55 g) dissolved in tetrahydrofuran (2 ml) dropwise at room temperature, the mixture was stirred at room temperature for one hour.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.25 g of the desired compound as a yellowish viscous oily product.

(12) Synthesis of methyl N-[2-[(6-chloro-2-methyl-2H-1,4-benzoxazin-3-ylthio)methyl]phenyl]-N-methoxy carbamate (Compound 90)

Potassium t-butoxide (0.12 g) was added to 6-chloro-2-methyl2H-1,4-benzoxazin-3-thione (0.25 g) dissolved in tetrahydrofuran (8 ml), and after adding methyl N-[2-(bromomethyl)phenyl]-N-methoxy carbamate (0.5 g) dissolved in tetrahydrofuran (3 ml) dropwise at room temperature, the mixture was stirred at room temperature for one hour.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.25 g of the desired compound as yellowish powder-like crystal.

(13) Synthesis of methyl N-[2-[(8-chloro-6-trifluoromethyl-2H-1,4-benzoxazin-3-ylthio)methyl] phenyl]-N-methoxy carbamate (Compound 103)

Potassium t-butoxide (0.25 g) was added to 8-chloro-6-trifluoromethyl-2H-1,4-benzoxazin-3-thione (0.5 g) dissolved in tetrahydrofuran (10 ml), and after adding methyl N-[2-(bromomethyl)phenyl]-N-methoxy carbamate (0.55 g) dissolved in tetrahydrofuran (5 ml) dropwise at room temperature, the mixture was stirred at room temperature for 2 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.70 g of the desired compound as yellowish powder-like crystal.

(14) Synthesis of methyl N-[2-[(6-chloro-8-methyl-2H-1,4-benzoxazin-3-ylthio)methyl]phenyl]-N-methoxy carbamate (Compound 104)

Potassium t-butoxide (0.20 g) was added to 6-chloro-8-methyl-2H-1,4-benzoxazin-3-thione (0.30 g) dissolved in tetrahydrofuran (8 ml), and after adding methyl N-[2-(bromomethyl)phenyl]-N-methoxy carbamate (0.35 g) dissolved in tetrahydrofuran (2 ml) dropwise at room temperature, the mixture was stirred at room temperature for 3 hours.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.35 g of the desired compound as pale yellowish powder-like crystal.

(15) Synthesis of methyl N-[2-[(6,8-dichloro-2H-1,4-benzoxazin-3-ylthio)methyl]phenyl]-N-methoxy carbamate (Compound 105)

Potassium t-butoxide (0.29 g) was added to 6,8-dichloro-2H-1,4-benzoxazin-3-thione (0.50 g) dissolved in tetrahydrofuran (10 ml), and after adding methyl N-[2-(bromomethyl)phenyl]-N-methoxy carbamate (0.5 g) dissolved in tetrahydrofuran (2 ml) dropwise at room temperature, the mixture was stirred at room temperature for one hour.

After completion of the reaction, the reaction mixture was poured into water (10 ml), and the desired compound was extracted with ethyl acetate. The extract was washed with a saturated saline solution and dried over anhydrous sodium sulfate, and the solvent was removed by distillation under reduced pressure.

The obtained residue was purified by silica gel chromatography (Wako gel C-200, eluted by toluene:ethyl acetate= 9:1) to obtain 0.60 g of the desired compound as pale yellowish powder-like crystal.

(16) Syntheses of other Compounds (1) in Table 3

According to the methods described in the above-mentioned (1) to (15), other Compounds (1) in Table 3 were synthesized.

Compounds synthesized as mentioned above are shown in Table 3, and physical properties thereof are shown in Table 4.

TABLE 3

(1)

| Compound | $R^1$ | $R^2$ | $R^3$ | $R^4$ | X | $(R^5)_n$ | Physical properties |
|---|---|---|---|---|---|---|---|
| 1 | H | $CH_3$ | H | H | O | H | m.p. 121~123° C. |
| 2 | $CH_3OCH_2$— | $CH_3$ | H | H | O | H | $n_D^{20}$ 1.5978 |
| 3 | H | $CH_3$ | $CH_3$ | $CH_3$ | O | H | Pale yellowish viscous liquid |
| 4 | $CH_3$ | $CH_3$ | $CH_3$ | $CH_3$ | O | H | $n_D^{20}$ 1.6052 |
| 5 | $C_2H_5$ | $CH_3$ | $CH_3$ | $CH_3$ | O | H | $n_D^{20}$ 1.5992 |
| 6 | n-$C_3H_7$ | $CH_3$ | $CH_3$ | $CH_3$ | O | H | $n_D^{20}$ 1.5928 |
| 7 | H | $CH_3$ | H | H | S | H | m.p. 106~109° C. |
| 8 | $CH_3OCH_2$— | $CH_3$ | H | H | S | H | $n_D^{20}$ 1.6255 |
| 9 | H | $CH_3$ | H | H | O | 6-$CH_3$ | m.p. 137~139° C. |
| 10 | $CH_3OCH_2$— | $CH_3$ | H | H | O | 6-$CH_3$ | $n_D^{27}$ 1.5994 |
| 11 | HC≡$CCH_2$— | $CH_3$ | H | H | O | 6-$CH_3$ | Yellowish viscous liquid |
| 12 | HC≡$CCH_2$— | $CH_3$ | $CH_3$ | H | O | 6-$CH_3$ | $n_D^{27}$ 1.5920 |
| 13 | $CH_3$ | $CH_3$ | $CH_3$ | $CH_3$ | O | 6-$CH_3$ | $n_D^{20}$ 1.6000 |
| 14 | $C_2H_5$ | $CH_3$ | $CH_3$ | $CH_3$ | O | 6-$CH_3$ | $n_D^{20}$ 1.5937 |
| 15 | n-$C_3H_7$ | $CH_3$ | $CH_3$ | $CH_3$ | O | 6-$CH_3$ | $n_D^{20}$ 1.5874 |
| 16 | H | $CH_3$ | H | H | O | 6-$C_2H_5$ | m.p. 107~108° C. |
| 17 | $CH_3OCH_2$— | $CH_3$ | H | H | O | 6-$C_2H_5$ | $n_D^{20}$ 1.5910 |
| 18 | HC≡$CCH_2$— | $CH_3$ | H | H | O | 6-$C_2H_5$ | Yellowish viscous liquid |
| 19 | H | $CH_3$ | H | H | O | 6-t-$C_4H_9$ | m.p. 123~125° C. |
| 20 | $CH_3OCH_2$— | $CH_3$ | H | H | O | 6-t-$C_4H_9$ | Pale yellowish viscouse liquid |
| 21 | HC≡$CCH_2$— | $CH_3$ | H | H | O | 6-t-$C_4H_9$ | Colorless viscous liquid |
| 22 | H | $CH_3$ | H | H | O | 6-$CF_3$ | m.p. 159~161° C. |
| 23 | $CH_3OCH_2$— | $CH_3$ | H | H | O | 6-$CF_3$ | Pale yellowish viscouse liquid |
| 24 | $CH_2$=$CHCH_2$— | $CH_3$ | H | H | O | 6-$CF_3$ | Yellowish viscouse liquid |
| 25 | HC≡$CCH_2$— | $CH_3$ | H | H | O | 6-$CF_3$ | Yellowish viscous liquid |
| 26 | H | $CH_3$ | H | H | O | 6-F | m.p. 145~147° C. |
| 27 | $CH_3OCH_2$— | $CH_3$ | H | H | O | 6-F | Pale yellowish viscouse liquid |
| 28 | HC≡$CCH_2$ | $CH_3$ | H | H | O | 6-F | Pale yellowish viscous liquid |
| 29 | H | $CH_3$ | H | H | O | 6-Cl | m.p. 156~157° C. |
| 30 | $CH_3OCH_2$— | $CH_3$ | H | H | O | 6-Cl | Yellowish viscous liquid |
| 31 | $C_2H_5OCH_2$— | $CH_3$ | H | H | O | 6-Cl | Pale yellowish viscouse liquid |
| 32 | $CH_2$=$CHCH_2$— | $CH_3$ | H | H | O | 6-Cl | Yellowish viscous liquid |
| 33 | HC≡$CCH_2$— | $CH_3$ | H | H | O | 6-Cl | Yellowish viscous liquid |
| 34 | $CH_3OCO$— | $CH_3$ | H | H | O | 6-Cl | m.p. 136~140° C. |
| 35 | H | $C_2H_5$ | H | H | O | 6-Cl | m.p. 133~136° C. |
| 36 | $CH_3OCH_2$— | $C_2H_5$ | H | H | O | 6-Cl | Yellowish viscous liquid |
| 37 | H | $CH_3$ | $CH_3$ | H | O | 6-Cl | m.p. 121~123° C. |

TABLE 3-continued

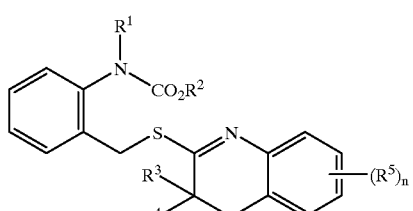

(1)

| Compound | $R^1$ | $R^2$ | $R^3$ | $R^4$ | X | $(R^5)_n$ | Physical properties |
|---|---|---|---|---|---|---|---|
| 38 | $CH_3OCH_2$— | $CH_3$ | $CH_3$ | H | O | 6-Cl | Pale yellowish viscouse liquid |
| 39 | $CH_3$ | $CH_3$ | $CH_3$ | H | O | 6-Cl | $n_D^{20}$ 1.5919 |
| 40 | $C_2H_5$ | $CH_3$ | $CH_3$ | H | O | 6-Cl | $n_D^{20}$ 1.6064 |
| 41 | n-$C_3H_7$ | $CH_3$ | $CH_3$ | H | O | 6-Cl | $n_D^{20}$ 1.6002 |
| 42 | H | $CH_3$ | $CH_3$ | $CH_3$ | O | 6-Cl | m.p. 125~127° C. |
| 43 | $CH_3OCH_2$— | $CH_3$ | $CH_3$ | $CH_3$ | O | 6-Cl | Colorless viscouse liquid |
| 44 | H | $CH_3$ | H | H | O | 6-Br | m.p. 166~168° C. |
| 45 | $CH_3OCH_2$— | $CH_3$ | H | H | O | 6-Br | Yellow brownish viscous liquid |
| 46 | HC≡$CCH_2$— | $CH_3$ | H | H | O | 6-Br | Pale yellowish viscouse liquid |
| 47 | H | $CH_3$ | H | H | O | 6-$NO_2$ | m.p. 158~160° C. |
| 48 | H | $CH_3$ | H | H | O | 6-CN | m.p. 176~179° C. |
| 49 | H | $CH_3$ | H | H | O | 5-$CH_3$ | Yellowish powder solid |
| 50 | $CH_3OCH_2$— | $CH_3$ | H | H | O | 5-$CH_3$ | Pale yellowish viscous liquid |
| 51 | H | $CH_3$ | H | H | O | 5-$NO_2$ | Yellowish powder solid |
| 52 | H | $CH_3$ | H | H | O | 7-$CH_3$ | m.p. 144~146° C. |
| 53 | $CH_3OCH_2$— | $CH_3$ | H | H | O | 7-$CH_3$ | Black reddish viscous liquid |
| 54 | HC≡$CCH_2$— | $CH_3$ | H | H | O | 7-$CH_3$ | Pale yellowish viscouse liquid |
| 55 | HC≡$CCH_2$— | $CH_3$ | $CH_3$ | H | O | 7-$NO_2$ | $n_D^{27}$ 1.5798 |
| 56 | $CH_3$ | $CH_3$ | $CH_3$ | $CH_3$ | O | 7-$NO_2$ | $n_D^{27}$ 1.6194 |
| 57 | H | $CH_3$ | H | H | O | 8-$CF_3$ | m.p. 79~80° C. |
| 58 | H | $CH_3$ | H | H | O | 8-CN | m.p. 133~135° C. |
| 59 | H | $CH_3$ | H | H | O | 6-Cl, 7-Cl | m.p. 217~218° C. |
| 60 | H | $CH_3$ | H | H | O | 6-Cl, 7-$C_2H_5$ | Pale yellowish powder solid |
| 61 | $CH_3OCH_2$— | $CH_3$ | H | H | O | 6-Cl, 7-$C_2H_5$ | $n_D^{20}$ 1.6030 |
| 62 | HC≡$CCH_2$— | $CH_3$ | H | H | O | 6-Cl, 7-$C_2H_5$ | Yellowish viscous liquid |
| 63 | H | $CH_3$ | H | H | O | 6-$CH_3$, 8-Cl | m.p. 164~166° C. |
| 64 | $CH_3OCH_2$— | $CH_3$ | H | H | O | 6-$CH_3$, 8-Cl | m.p. 94~97° C. |
| 65 | HC≡$CCH_2$— | $CH_3$ | H | H | O | 6-$CH_3$, 8-Cl | m.p. 121~123° C. |
| 66 | HC≡$CCH_2$— | $CH_3$ | H | H | O | 6-$C_2H_5$, 8-Cl | m.p. 70~72° C. |
| 67 | H | $CH_3$ | H | H | O | 6-$CF_3$, 8-Cl | m.p. 167~68° C. |
| 68 | $CH_3OCH_2$— | $CH_3$ | H | H | O | 6-$CF_3$, 8-Cl | m.p. 95~97° C. |
| 69 | HC≡$CCH_2$— | $CH_3$ | H | H | O | 6-$CF_3$, 8-Cl | m.p. 101~103° C. |
| 70 | H | $CH_3$ | H | H | O | 6-F, 8-F | m.p. 164~167° C. |
| 71 | $CH_3OCH_2$— | $CH_3$ | H | H | O | 6-F, 8-F | $n_D^{20}$ 1.5724 |
| 72 | $CH_3OCH_2$— | $CH_3$ | H | H | O | 6-F, 8-Cl | m.p. 93~95° C. |
| 73 | H | $CH_3$ | H | H | O | 6-Cl, 8-Cl | m.p. 171~173° C. |
| 74 | $CH_3OCH_2$— | $CH_3$ | H | H | O | 6-Cl, 8-Cl | m.p. 113~115° C. |
| 75 | HC≡$OCH_2$— | $CH_3$ | H | H | O | 6-Cl, 8-Cl | m.p. 129~131° C. |
| 76 | H | $CH_3$ | H | H | O | 6-Cl, 8-$CH_3$ | m.p. 152~154° C. |
| 77 | HC≡$CCH_2$— | $CH_3$ | H | H | O | 6-Cl, 8-$CH_3$ | Yellowish viscous liquid |
| 78 | H | $CH_3$ | H | H | O | 7-F, 8-F | Pale brownish powder solid |
| 79 | $CH_3OCH_2$— | $CH_3$ | H | H | O | 7-F, 8-F | $n_D^{20}$ 1.5855 |
| 80 | H | $CH_3$ | H | H | O | 5-Cl, 6-Cl, 8-Cl | m.p. 178~180° C. |
| 81 | HC≡$CCH_2$— | $CH_3$ | H | H | O | 5-Cl, 6-Cl, 8-Cl | m.p. 149~151° C. |
| 82 | $C_2H_5$ | $CH_3$ | H | H | O | 6-$C_2H_5$, 8-Cl | Pale yellowish viscouse liquid |
| 83 | $CH_3O$ | $CH_3$ | H | H | O | H | Pale yellowish viscouse liquid |
| 84 | $CH_3O$ | $CH_3$ | H | H | S | H | Dark reddish viscouse liquid |

TABLE 3-continued

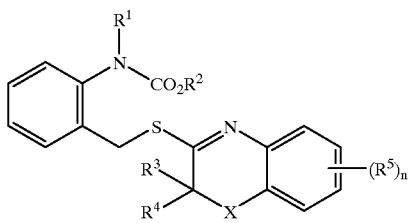

(1)

| Compound | $R^1$ | $R^2$ | $R^3$ | $R^4$ | X | $(R^5)_n$ | Physical properties |
|---|---|---|---|---|---|---|---|
| 85 | $CH_3O$ | $CH_3$ | H | H | O | 6-$CH_3$ | Yellow brownish viscous liquid |
| 86 | $CH_3O$ | $CH_3$ | H | H | O | 6-t-$C_4H_9$ | Orange viscouse liquid |
| 87 | $CH_3O$ | $CH_3$ | H | H | O | 6-$CF_3$ | Brownish viscouse liquid |
| 88 | $CH_3O$ | $CH_3$ | H | H | O | 6-F | Yellowish viscous liquid |
| 89 | $CH_3O$ | $CH_3$ | H | H | O | 6-Cl | $n_D^{20}$ 1.6064 |
| 90 | $CH_3O$ | $CH_3$ | $CH_3$ | H | O | 6-Cl | Orange viscous liquid |
| 91 | $CH_3O$ | $CH_3$ | $CH_3$ | $CH_3$ | O | 6-Cl | Orange viscous liquid |
| 92 | $CH_3O$ | $CH_3$ | H | H | O | 6-Br | Yellowish viscous liquid |
| 93 | $CH_3O$ | $CH_3$ | H | H | O | 6-$NO_2$ | Orange viscous liquid |
| 94 | $CH_3O$ | $CH_3$ | H | H | O | 7-$CH_3$ | Orange viscous liquid |
| 95 | $CH_3O$ | $CH_3$ | H | H | O | 7-$NO_2$ | m.p. 115~118° C. |
| 96 | $CH_3O$ | $CH_3$ | H | H | O | 5-Cl, 6-Cl | Pale brownish viscous liquid |
| 97 | $CH_3O$ | $CH_3$ | H | H | O | 6-Cl, 7-$CH_3$ | Orange viscous liquid |
| 98 | $CH_3O$ | $CH_3$ | H | H | O | 6-Cl, 7-$C_2H_5$ | Pale yellowish viscous liquid |
| 99 | $CH_3O$ | $CH_3$ | H | H | O | 6-Cl, 7-Cl | Pale yellowish viscous liquid |
| 100 | $CH_3O$ | $CH_3$ | H | H | O | 6-Cl, 7-$NO_2$ | m.p. 120~123° C. |
| 101 | $CH_3O$ | $CH_3$ | H | H | O | 6-$CH_3$, 8-Cl | m.p. 118~121° C. |
| 102 | $CH_3O$ | $CH_3$ | H | H | O | 6-$C_2H_5$, 8-Cl | m.p. 71~73° C. |
| 103 | $CH_3O$ | $CH_3$ | H | H | O | 6-$CF_3$, 8-Cl | m.p. 113~115° C. |
| 104 | $CH_3O$ | $CH_3$ | H | H | O | 6-Cl, 8-$CH_3$ | m.p. 99~101° C. |
| 105 | $CH_3O$ | $CH_3$ | H | H | O | 6-Cl, 8-Cl | m.p. 81~83° C. |
| 106 | $CH_3O$ | $CH_3$ | H | H | O | 5-Cl, 6-Cl, 8-Cl | m.p. 156~159° C. |
| 107 | $C_2H_5O$ | $CH_3$ | H | H | O | 6-Cl | Pale yellowish viscous liquid |
| 108 | $C_2H_5O$ | $CH_3$ | H | H | O | 6-$CF_3$ | $n_D^{20}$ 1.5528 |
| 109 | $C_2H_5O$ | $CH_3$ | H | H | O | 6-$CF_3$, 8-Cl | m.p. 102~103° C. |
| 110 | $C_2H_5O$ | $CH_3$ | H | H | O | 6-Cl, 8-$CH_3$ | m.p. 89~92° C. |
| 111 | $C_2H_5O$ | $CH_3$ | H | H | O | 6-Cl, 8-Cl | m.p. 123~125° C. |
| 112 | $CH_3O$ | $C_2H_5$ | H | H | O | 6-Cl | $n_D^{20}$ 1.5928 |
| 113 | $CH_3O$ | $C_2H_5$ | H | H | O | 6-$CF_3$, 8-Cl | $n_D^{20}$ 1.5655 |
| 114 | $CH_3O$ | $CH_3$ | H | H | O | 6-$C_5H_{11}$-n, 8-Cl | |
| 115 | HC≡$CCH_2$— | $CH_3$ | H | H | O | 6-Ph | See Table 4 |
| 116 | $CH_3O$ | $CH_3$ | H | H | O | 6-Cl, 8-$C_2H_5$ | See Table 4 |
| 117 | $CH_3O$ | $CH_3$ | H | H | O | 6-Cl, 8-$C_2H_5$ | See Table 4 |
| 118 | $CH_3O$ | $CH_3$ | H | H | O | 6-$COC_2H_5$, 8-Cl | |
| 119 | $CH_3O$ | $CH_3$ | H | H | O | 5-$CF_3$, 6-F | $n_D^{23.8}$ 1.5822 |
| 120 | $CH_3O$ | $CH_3$ | H | H | O | 6-F, 7-$CF_3$ | $n_D^{24}$ 1.5656 |
| 121 | $CH_3O$ | $CH_3$ | H | H | O | 6-$SO_2C_2H_5$ | $n_D^{24.3}$ 1.5735 |
| 122 | $CH_3O$ | $CH_3$ | H | H | O | 6-$COOC_3H_7$-i | |
| 123 | $CH_3O$ | $CH_3$ | H | H | O | 6-$OCF_3$, 8-Cl | See Table 4 |
| 124 | HC≡$CCH_2$— | $CH_3$ | H | H | O | 6-$OCF_3$, 8-Cl | See Table 4 |
| 125 | HC≡$CCH_2$— | $CH_3$ | H | H | O | 6-$OCF_3$ | See Table 4 |
| 126 | $CH_3O$ | $CH_3$ | H | H | O | 6-Cl, 8-$C_3H_7$-n | See Table 4 |
| 127 | $CH_3$ | $CH_3$ | H | H | O | 6-$C_5H_{11}$-n, 8-Cl | |
| 128 | HC≡$CCH_2$— | $CH_3$ | H | H | O | 6-F, 7-$CF_3$ | See Table 4 |
| 129 | $CH_3O$ | $C_2H_5$ | H | H | O | 6-$OCF_3$ | See Table 4 |
| 130 | HC≡$CCH_2$— | $CH_3$ | H | H | O | 6-Ph | See Table 4 |
| 131 | HC≡$CCH_2$— | $CH_3$ | H | H | O | 5-$CF_3$, 6-F | See Table 4 |
| 132 | HC≡$CCH_2$— | $CH_3$ | H | H | O | 6-$SO_2C_2H_5$ | See Table 4 |
| 133 | $CH_3O$ | $CH_3$ | H | H | O | 6-Cl, 8-$C_5H_{11}$-n | See Table 4 |

TABLE 3-continued (1)

| Compound | R¹ | R² | R³ | R⁴ | X | (R⁵)ₙ | Physical properties |
|---|---|---|---|---|---|---|---|
| 134 | HCCCH₂— | CH₃ | H | H | O | 6-Cl, 8-C₅H₁₁-n | See Table 4 |
| 135 | CH₃O | CH₃ | H | H | O | 6-C₄H₉-n | See Table 4 |
| 136 | CH₃O | CH₃ | H | H | O | 6-C₅H₁₁-n | See Table 4 |
| 137 | CH₃O | CH₃ | H | H | O | 6-C₆H₁₃-n | See Table 4 |
| 138 | CH₃O | CH₃ | H | H | O | 6-CO₂-Benzyl, 8-Cl | m.p. 111~112° C. |
| 139 | CH₃O | CH₃ | H | H | O | 6-CO₂CH₃, 8-Cl | m.p. 106~107° C. |
| 140 | CH₃O | CH₃ | H | H | O | 6-Cl, 8-CO—C₄H₉-n | $n_D^{23.2}$ 1.5950 |
| 141 | HC≡CCH₂— | CH₃ | H | H | O | 6-COC₂H₅, 8-Cl | m.p. 145~147° C. |
| 142 | CH₃ | CH₃ | H | H | O | 6-CF₃ | $n_D^{20.3}$ 1.5808 |
| 143 | CH₃ | CH₃ | H | H | O | 6-C₂H₅, 8-Cl | $n_D^{20.4}$ 1.6070 |
| 144 | CH₃ | CH₃ | H | H | O | 6-Cl | See Table 4 |
| 145 | CH₃ | CH₃ | H | H | O | 6-CH₃, 8-Cl | See Table 4 |
| 146 | CH₃O | CH₃ | H | H | O | 6-C₄H₉-n, 8-Cl | $n_D^{20.0}$ 1.5948 |
| 147 | CH₃O | CH₃ | H | H | O | 6-C₃H₇-n, 8-Cl | $n_D^{20.0}$ 1.5848 |

TABLE 4

| Compound | Physical properties: ¹H—NMR (CDCl₃, δ value, ppm) |
|---|---|
| 8 | 3.24(s, 2H), 3.48(s, 3H), 3.70(s, 3H), 4.40~4.54(m, 2H), 4.98(dd, 2H), 7.03~7.11(m, 1H), 7.15~7.36(m, 6 H), 7.57~7.60(m, H) |
| 10 | 2.32(s, 3H), 3.47(s, 3H), 3.70(s, 3H), 4.37~4.51 (m, 4H) 4.40(s, 2H), 4.46(s, 2H), 6.77(d, 1H), 6.85~6.91(m, 1H), 7.10~7.34(m, 4H), 7.54~7.59(m, 1H) |
| 17 | 1.23(t, 3H), 2.61(q, 2H), 3.48(s, 3H), 3.70(s, 3H), 4.37~4.60(m, 4H), 4.99(dd, 2H), 6.79(d, 1H), 6.88~6.92(m, 1H), 7.12~7.43(m, 4H), 7.52~7.60(m, 1H) |
| 18 | 1.25(t, 3H), 2.30(s, 1H), 2.60(q, 2H), 3.69(s, 3H), 4.37~4.50(m, 4H), 4.60(s, 2H), 6.79(d, 1H), 6.87~6.93(m, 1H), 7.13~7.37(m, 3H), 7.47(d, 1H), 7.55~7.61(m, 1H) |
| 20 | 1.33(s, 9H), 3.48(s, 3H), 3.71(s, 3H), 4.38~4.53(m, 4H), 4.98(dd, 2H), 6.81(d, 1H), 7.08~7.33(m, 5H), 7.54~7.59(m, 1H) |
| 21 | 1.33(s, 9H), 2.30(s, 1H), 3.70(s, 3H), 4.39~4.52(m, 4H), 4.57(s, 2H), 6.81(d, 1H), 7.10(d, 1H), 7.26~7.33(m, 3H), 7.40(s, 1H), 7.57~7.62(m, 1H) |
| 23 | 3.48(s, 3H), 3.71(s, 3H), 4.40~4.59(m, 4H), 4.98(dd, 2H), 6.96(d, 1H), 7.15~7.36(m, 4H), 7.54~7.58(m, 1H) |
| 24 | 3.61(d, 2H), 3.71(s, 3H), 4.35~4.60(m, 2H), 5.01~5.17(m, 4H), 5.67~5.83(m, 1H), 6.92~6.99(m, 1H), 7.15~7.49(m, 4H), 7.52~7.59(m, 2H) |
| 25 | 2.30(s, 1H), 3.70(s, 3H), 4.20~4.65(m, 4H), 4.55(s, 2H), 6.96(d, 1H), 7.11~7.42(m, 4H), 7.51~7.60(m, 2H) |
| 27 | 3.47(s,3H), 3.70(s, 3H), 4.35~4.51(m, 4H), 4.98(dd, 2H), 6.73~6.85(m, 2H), 7.00~7.05(m, 1H), 7.20~7.35(m, 3H), 7.52~7.59(m, 1H) |
| 28 | 2.30(s, 1H), 3.70(s, 3H), 4.20~4.63(m, 4H), 4.46(s, 2H), 6.73~6.86(m, 2H), 6.99~7.05(m, 1H), 7.28~7.40(m, 2H), 7.51~7.60(m, 1H) |
| 30 | 3.48(s, 3H), 3.70(s, 3H), 4.37~4.51(m, 4H), 4.98(dd, 2H), 6.80(d, 1H), 7.01~7.07(m, 1H), 7.19~7.35(m, 4H), 7.51~7.58(m, 1H) |
| 32 | 3.60(d, 2H), 3.71(s, 3H), 4.32~4.52(m, 2H), 5.00~5.10(m, 4H) 5.68~5.82(m, 1H), 6.78~6.84(m, 1H), 6.95~7.0 5(m, 2H), 7.15~7.22(m, 2H), 7.32~7.46(m, 2H) |
| 33 | 2.30(s, 1H), 3.71(s, 3H), 4.42~4.62(m, 4H), 4.47(s, 2H), 6.81(d, 1H), 7.00~7.06(m, 1H), 7.22~7.38(m, 4H), 7.52~7.59(m, 1H) |
| 34 | 3.77(s, 6H) 4.40(s, 2H), 4.46(s, 2H), 6.81(d, 1H), 7.03(dd, 1H), 7.12~7.19(m, 1H), 7.22~7.38(m, 3H), 7.51~7.58(m, 1H) |
| 36 | 1.21(b, 3H) 3.48(s, 3H), 4.19(b, 3H), 4.42(s, 2H) 4.47(s, 2H), 4.98(dd, 2H), 6.80(d, 1H), 7.01~7.06 (m, 1H), 7.15~7.34(m, 4H), 7.50~7.56(m, 1H) |
| 38 | 1.46(d, 3H), 3.48(s, 3H), 3.70(s, 3H), 4.31~4.47(m, 2H), 4.59(q, 1H), 4.97(dd, 2H), 6.80(d, 1H), 7.03(dd, 1H), 7.21~7.32(m, 4H), 7.50~7.57(m, 1H) |
| 43 | 1.47(s, 6H), 3.48(s, 3H), 3.71(s, 3H), 4.36(dd, 2H), 4.98(dd, 2H), 6.79(d, 1H), 7.00~7.01(m, 1H), 7.43~7.34(m, 4H), 7.49~7.56(m, 1H) |
| 45 | 3.47(dd, 3H), 3.71(s, 3H), 4.42(dd, 2H), 4.48(s, 2H), 4.98(dd, 2H), 6.77(d, 1H), 7.15~7.34(m, 4H), 7.43(s, 1H), 7.52~7.57(m, 1H) |
| 46 | 2.30(s, 1H), 3.70(s, 3H), 4.20~4.64(m, 4H), 4.48(s, 2H), 6.77(d, 1H), 7.14~7.20(m, 2H), 7.30~7.36(m, 2H), 7.44(d, 1H), 7.52~7.60(m, 1H) |
| 50 | 2.47(s, 3H), 3.46(s, 3H), 3.70(s, 3H), 4.40~4.49(m, 4H), 4.98(dd, 2H), 6.73(d, 1H), 6.86(d, 1H), 6.95~6.99(m, 1H), 7.16~7.32(m, 3H), 7.60(d, 1H) |
| 51 | 3.75(d, 3H), 3.80(s, 3H), 4.70(s, 3H), 7.05~7.11(m, 2H), 7.19~7.33(m, 4H), 7.92(d, 1H), 10.05(b, 1H) |
| 53 | 2.31(s, 3H), 3.48(s, 3H), 3.69(s, 3H), 4.36~4.50(m, 4H), 4.99(dd, 2H), 6.70(s, 1H), 6.78~6.85(m, 2H), 7.12~7.31(m, 3H), 7.52~7.57(m, 1H) |
| 54 | 2.30(s, 1H), 2.31(s, 3H), 3.69(s, 3H), 4.14~4.66(m, 4H), 4.44(s, 2H), 6.70(s, 1H), 6.80(d, 1H), 7.14~7.33(m, 4H), 7.54~7.60(m, 1H) |
| 57 | 3.82(s, 3H), 4.35(s, 2H), 4.55(s, 2H), 7.01~7.20(m, 2H), 7.21~7.30(m, 11H), 7.40(s, 1H), 7.91~7.99(m, 2H), 9.10(s, 1H) |
| 61 | 1.21(t, 3H), 2.69(q, 2H), 3.48(s, 3H), 3.70(s, 3H), 4.39~4.48(m, 4H), 4.98(dd, 2H), 6.76(d, 1H), 7.14~7.36(m, 4H), 7.52~7.59(m, 1H) |
| 62 | 1.21(t, 3H), 2.30(s, 1H), 2.70(q, 2H), 3.70(s, 3H), |

TABLE 4-continued

| Compound | Physical properties: ¹H—NMR (CDCl₃, δ value, ppm) |
|---|---|
|  | 4.20~4.62(m, 4H), 4.46(s, 2H), 6.76(s, 1H), 7.22~7.39(m, 4H), 7.52~7.59(m, 1H) |
| 65 | 2.30(s, 1H), 2.30(s, 3H), 3.70(s, 3H), 4.20~4.63(m, 4H), 4.56(s, 2H), 6.97(s, 1H), 7.02(s, 1H), 7.29~7.38(m, 3H), 7.53~7.60(m, 1H) |
| 66 | 1.24(t, 3H), 2.30(s, 1H), 2.60(q, 2H), 3.70(s, 3H), 4.20~4.62(m, 4H), 4.54(s, 2H), 6.99(d, 1H), 7.04(s, 1H), 7.29~7.37(m, 3H), 7.52~7.60(m, 1H) |
| 68 | 3.47(s, 3H), 3.71(s, 3H), 4.39~4.52(m, 2H), 4.65(s, 2H), 4.98(dd, 2H), 7.15~7.39(m, 3H), 7.42(s, 1H), 7.48(s, 1H), 7.51~7.57(m, 1H) |
| 69 | 2.30(s, 3H), 3.71(s, 3H), 4.23~4.60(m, 4H), 4.66(s, 2H), 7.30~7.36(m, 3H), 7.41(s, 1H), 7.47(s, 1H), 7.51~7.58(m, 1H) |
| 71 | 3.48(s, 3H), 3.70(s, 3H), 4.38~4.52(m, 4H), 4.98(dd, 2H), 6.63~6.72(m, 1H), 6.82~6.90(m, 1H), 7.15~7.37(m, 3H), 7.49~7.57(m, 1H) |
| 72 | 3.47(s, 3H), 3.70(s, 3H), 4.39~4.51(m, 2H), 4.54(s, 2H), 4.98(dd, 2H), 6.89~7.00(m, 2H), 7.51~7.56(m, 1H), 7.20~7.37(m, 3H) |
| 74 | 3.48(s, 3H), 3.70(s, 3H), 4.44(s, 2H), 4.57(s, 2H), 4.97(dd, 2H), 7.12(d, 1H), 7.20~7.45(m, 4H), 7.49~7.55(m, 1H) |
| 75 | 2.30(s, 1H), 3.70(s, 3H), 4.20~4.64(m, 4H), 4.58(s, 2H), 7.12(s, 1H), 7.20(s, 1H), 7.28~7.40(m, 3H), 7.51~7.59(m, 1H) |
| 77 | 2.17(s, 3H), 2.30(s, 1H), 3.69(s, 3H), 4.33~4.63(m, 4H), 4.49(s, 2H), 6.92(s, 1H), 7.06~7.33(m, 3H), 7.47(s, 1H), 7.52~7.60(m, 1H) |
| 81 | 2.31(s, 1H), 3.71(s, 3H), 4.15~4.62(m, 4H), 4.56(s, 2H), 7.26~7.40(m, 4H), 7.69~7.73(m, 1H) |
| 83 | 3.77(s, 3H), 3.80(s, 3H), 4.48(s, 2H), 4.54(s, 2H), 6.89(d, 1H), 6.97~7.11(m, 2H), 7.28~7.36(m, 4H), 7.60~7.67(m, 1H) |
| 84 | 3.21(s, 2H), 3.78(s, 3H), 3.80(s, 3H), 4.53(s, 2H), 7.02~7.10(m, 1H), 7.15~7.29(m, 3H), 7.30~7.38(m, 3H), 7.60~7.65(m, 1H) |
| 85 | 2.31(s, 3H), 3.78(ds, 3H), 3.81(s, 3H), 4.44(s, 2H), 4.52(s, 2H), 6.78(d, 1H), 6.89(dd, 1H), 7.12(d, 1H), 7.30~7.39(m, 3H), 7.60~7.65(m, 1H) |
| 86 | 1.32(s, 9H), 3.78(s, 3H), 3.81(s, 3H), 4.46(s, 2H), 4.55(s, 2H), 6.81(d, 1H), 7.11(dd, 1H), 7.30~7.35(m, 4H), 7.59~7.64(m, 1H) |
| 87 | 3.78(s, 3H), 3.81(s, 3H), 4.53(s, 2H), 4.54(s, 2H), 6.96(d, 1H), 7.30~7.40(m, 4H), 7.57(d, 1H), 7.58~7.63(m, 1H) |
| 88 | 3.78(s, 3H), 3.81(s, 3H), 4.46(s, 2H), 4.52(s, 2H), 6.75~6.85(m, 2H), 7.02(dd, 1H), 7.28~7.38(m, 3H), 7.58~7.62(m, 1H) |
| 89 | 3.77(s, 3H), 3.81(s, 3H), 4.47(s, 2H), 4.51(s, 2H), 6.81(d, 1H), 7.03(dd, 1H), 7.28~7.37(m, 4H), 7.58~7.63(m, 1H) |
| 90 | 1.45(d, 3H), 3.78(s, 3H), 3.81(s, 3H), 4.49(s, 2H), 4.60(q, 1H), 6.81(d, 1H), 7.03(dd, 1H), 7.24~7.37(m, 4H), 7.56~7.62(m, 1H) |
| 91 | 1.47(s, 6H), 3.78(s, 3H), 3.81(s, 3H), 4.45(s, 2H), 6.79(d, 1H), 7.03(dd, 1H), 7.25~7.36(m, 4H), 7.53~7.59(m, 1H) |
| 92 | 3.77(s, 3H), 3.81(s, 3H), 4.47(s, 2H), 4.51(s, 2H), 6.76(d, 1H), 7.12~7.20(m, 1H), 7.29~7.36(m, 3H), 7.42~7.45(m, 1H), 7.57~7.61(m, 1H) |
| 93 | 3.79(s, 3H), 3.82(s, 3H), 4.54(s, 2H), 4.62(s, 2H), 6.96(d, 1H), 7.22~7.28(m, 2H), 7.31~7.36(m, 2H), 7.59~7.64(m, 1H), 8.00(dd, 1H) |
| 94 | 2.31(s, 3H), 3.78(s, 3H), 3.80(s, 3H), 4.45(s, 2H), 4.53(s, 2H), 6.70(s, 1H), 6.80(s, 1H), 8.16~7.20(m, 1H), 7.30~7.33(m, 3H), 7.58~7.64(m, 1H) |
| 95 | 3.78(s, 3H), 3.82(s, 3H), 4.56(s, 2H), 4.58(s, 2H), 7.30~7.36(m, 3H), 7.40(d, 1H), 7.57~7.62(m, 1H), 7.77(s, 1H), 7.91(dd, 1H) |
| 96 | 3.78(s, 3H), 3.81(s, 3H), 4.45(s, 2H), 4.61(s, 2H), 6.78(s, 1H), 7.16(d,1H), 7.28~7.38(m, 3H), 7.79~7.84(m, 1H) |
| 98 | 1.22(s, 2H), 2.69(q, 2H), 3.78(s, 3H), 3.81(s, 3H), 4.46(s, 2H), 4.51(s, 2H), 6.77(s, 1H), 7.29~7.35(m, 4H), 7.57~7.62(m, 1H) |
| 99 | 3.76(s, 3H), 3.80(s, 3H), 4.58(s, 2H), 4.61(s, 2H), 6.99(s, 1H), 7.29~7.39(m, 4H), 7.55~7.61(m, 1H) |
| 100 | 3.77(s, 3H), 3.82(s, 3H), 4.54(s, 2H), 4.57(s, 2H), 7.32~7.35(m, 3H), 7.45(s, 1H), 7.51(s, 1H), 7.54~760(m, 2H) |
| 101 | 2.30(s, 3H), 3.77(s, 3H), 3.81(s, 3H), 4.52(s, 2H), 4.54(s, 2H), 6.97(s, 1H), 7.04(s, 1H), 7.22~7.40(m, 3H), 7.56~7.64(m, 1H) |
| 102 | 1.24(t, 3H), 2.59(q, 2H), 3.78(s, 3H), 3.81(s, 3H), 4.52(s, 2H), 4.54(s, 2H), 6.99(s, 1H), 7.06(s, 1H), 7.27~7.36(m, 3H), 7.57~7.62(m, 1H) |
| 103 | 3.78(s, 3H), 3.81(s, 3H), 4.53(s, 2H), 4.64(s, 2H), 7.28~7.38(m, 3H), 7.41(s, 1H), 7.48(s, 1H), 7.55~7.61(m, 1H) |
| 104 | 2.18(5, 3H), 3.78(s, 3H), 3.81(s, 3H), 4.48(s, 2H), 4.51(s, 2H), 6.92(d, 1H), 7.14(d, 1H), 7.29~7.35(m, 3H), 7.58~7.63(m, 1H) |
| 105 | 3.77(s, 3H), 3.82(s, 3H), 4.51(s, 2H), 4.58(s, 2H), 7.14(d, 1H), 7.22(d, 1H), 7.30~7.38(m, 3H), 7.55~7.61(m, 1H) |
| 107 | 1.27(t, 3H), 3.80(s, 3H), 4.00(q, 2H), 4.47(s, 2H), 4.52(s, 2H), 6.80(d, 1H), 7.02(dd, 1H), 7.27~7.38(m, 4H), 7.56~7.62(m, 1H) |
| 108 | 1.27(d, 3H), 3.80(s, 3H), 4.01(q, 2H), 4.54(s, 4H), 6.96(d, 1H), 7.17~7.21(m, 1H), 7.28~7.39(m, 3H), 7.56(d, 1H), 7.58~7.62(m, 1H) |
| 109 | 1.27(t, 3H), 3.80(s, 3H), 4.00(q, 2H), 4.53(s, 2H), 4.64(s, 2H), 7.29~7.38(m, 3H), 7.41(s, 1H), 7.47(s, 1H), 7.54~7.60(m, 1H) |
| 110 | 1.27(t, 3H), 2.18(s, 3H), 3.81(s, 3H), 4.00(q, 2H), 4.48(s, 2H), 4.51(s, 2H), 6.91(d, H), 7.13(d, 1H), 7.25~7.38(m, 3H), 7.58~7.61(m, 1H) |
| 111 | 1.26(t, 3H), 3.80(s, 3H), 4.00(q, 2H), 4.52(s, 2H), 4.58(s, 2H), 7.14(s, 1H), 7.20(s, 1H), 7.29~7.35(m, 3H), 7.54~7.60(m, 1H) |
| 112 | 1.30(t, 3H), 3.78(s, 3H), 4.27(q, 2H), 4.46(s, 2H), 4.51(s, 2H), 6.80(d, 1H), 7.02(dd, 1H), 7.28~7.35(m, 4H), 7.57~7.61(m, 1H) |
| 113 | 1.31(t, 3H), 3.78(s, 3H), 4.28(q, 2H), 4.54(s, 2H), 4.64(s, 2H), 7.27~7.36(m, 3H), 7.41(s, 1H), 7.48(s, 1H), 7.55~7.61(m, 1H) |
| 115 | 3.78(s, 3H), 3.81(s, 3H), 4.52(s, 2H), 4.55(s, 2H), 6.90~7.70(m, 12H) |
| 116 | 1.17(t, 3H), 2.57(q, 2H), 3.77(s, 3H), 3.81(s, 3H), 4.46(s, 3H), 4.51(s, 2H), 6.93(d, 1H), 7.15(d, 1H), 7.30~7.38(m, 3H), 7.60(m, 1H) |
| 117 | 1.17(t, 3H), 2.30(t, 1H), 2.57(q, 2H), 3.69(s, 3H), 4.27(d, 1H), 4.46(s, 2H), 4.49(d, 1H), 4.58(d, 1H), 6.94(d, 1H), 7.12~7.36(m, 4H), 7.57(m, 1H) |
| 123 | 3.77(s, 3H), 3.81(s, 3H), 4.52(s, 2H), 4.59(s, 2H), 7.01~7.62(m, 6H) |
| 124 | 2.04(s, 1H), 3.63~3.84(br s , 3H), 4.32~4.48(m, 2H), 4.58(s, 2H), 4.98~5.10(m, 2H), 7.00~7.57(m, 6H) |
| 125 | 2.26~2.32(s, 1H, J=2.4Hz), 3.54~3.77(br s , 3H), 4.19~4.64(m, 6H), 6.78~7.61(m, 7H) |
| 126 | 0.93(t, 3H), 1.57(t, 2H), 2.52(q, 2H), 3.77(br s, 3H), 3.81(s, 3H), 4.45(s, 2H), 4.51(s, 2H), 6.91(d, 1H), 7.11~7.39(m, 4H), 7.61(m, 1H) |
| 128 | 3.53~3.86(br s, 3H), 4.43(s, 2H), 4.49(s, 2H), 4.96~5.10(m, 2H), 7.04~7.44(m, 5H), 7.48~7.59(m, 1H) |
| 129 | 3.77(s, 3H), 3.86(br s, 3H), 4.49(s, 2H), 4.52(s, 2H), 6.90~7.70(m, 4H), 7.61(m, 12H) |
| 130 | 2.26~2.31(m, 1H), 3.60~3.77(br s, 3H), 4.23~4.45(m, 2H), 4.52(s, 2H), 4.5(s, 2H), 6.91~7.67(m, 12H) |
| 131 | 3.61~3.84(br s, 3H), 4.42~4.46(m, 2H), 4.47(s, 2H), 4.96~5.16(m, 2H), 6.88(dd, 1H, J=10.2, J=8.8Hz), 7.40(dd, 1H, J=4.4, JF=8.8Hz), 7.09~7.18(m, 1H), 7.27~7.43(m, 2H), 7.51~7.57(m, 1H) |
| 132 | 1.31(t, 3H, J=7.4Hz), 2.04(s, 1H), 3.14(q, 2H, J=7.4Hz), 3.64~3.81(brs, 3H), 4.35~4.48(m, 2H), 4.59(s, 2H), 5.01~5.11(m, 2H), 7.01(d, 1H, J=8.3Hz), 7.10~7.20(m, 2H), 7.22~7.29(m, 1H), 7.49~7.57(m, 1H), 7.62(dd, 1H, JF=8.3, J=2.4Hz), 7.84(d, 1H, J=2.4Hz) |
| 133 | 0.89(t, 3H), 1.32(m, 4H), 1.54(m, 2H), 2.53(t, 2H), 3.77(s, 3H), 3.81(s, 3H), 4.45(s, 2H), 4.51(s, 2H), 6.91(d, 1H), 7.11~7.35(m, 4H), 7.60(m, 1H) |

TABLE 4-continued

| Compound | Physical properties: $^1$H—NMR (CDCl$_3$, δ value, ppm) |
|---|---|
| 134 | 0.89(t, 3H), 1.31(m, 4H), 1.54(m, 2H), 2.30(t, 1H), 2.53(t, 3H), 3.70(br s, 3H), 4.27(d, 1H), 4.45(s, 2H), 4.48(d, 1H), 4.58(d, 1H), 6.92(d, 1H), 7.14(d, 1H), 7.33(m, 3H), 7.57(m, 1H) |
| 135 | 0.94(t, 3H), 1.37(m, 2H), 1.60(m, 2H), 2.58(t, 2H), 3.77(s, 3H), 3.81(s, 3H), 4.45(s, 2H), 4.52(s, 2H), 6.79(d, 1H), 6.89(dd, 1H), 7.13(d, 1H), 7.14~7.35 (m, 4H), 7.62(m, 1H) |
| 136 | 0.90(t, 3H), 1.33(m, 4H), 1.61(m, 2H), 2.57(t, 2H), 3.77(s, 3H), 3.81(s, 3H), 4.45(s, 2H), 4.52(s, 2H), 6.79(d, 1H), 6.89(dd, 1H), 7.13(d, 1H), 7.15~7.35 (m, 4H), 7.63(m, 1H) |
| 137 | 0.89(t, 3H), 1.32(m, 6H), 1.61(m, 2H), 2.57(t, 2H), 3.77(s, 3H), 3.81(s, 3H), 4.45(s, 2H), 4.52(s, 2H), 6.78(d, 1H), 6.89(dd, 1H), 7.12(d, 1H), 7.15~7.35 (m, 4H), 7.63(m, 1H) |
| 144 | 3.25~3.28(s, 3H), 3.63(s, 3H), 3.83(d, 2H), 4.48(m, 2H), 6.79(d, 1H), 6.92~6.96(m, 2H), 7.01~7.05(m, 2H), 7.39~7.32(m, 2H) |
| 145 | 2.30~2.35(m, 3H), 3.25~3.27(m, 3H), 3.65(d, 3H) 3.97(s, 2H), 4.47~4.54(m, 2H), 6.81(d, 1H), 7.05(s, 1H), 7.17(d, 2H), 7.54(d, 1H), 7.87(s, 1H) |

Example 2 (Preparation of formulation)

(1) Preparation of granule

Five parts by weight of Compound 7, 35 parts by weight of bentonite, 57 parts by weight of talc, 1 part by weight of Neopelex powder (trade name, produced by Kao K.K.) and 2 parts by weight of sodium lignosulfonate were uniformly mixed, and then, the mixture was kneaded with addition of a small amount of water, followed by granulation and drying, to obtain a granule.

(2) Preparation of wettable powder

Ten parts by weight of Compound 7, 67.5 parts by weight of kaolin, 20 parts by weight of white carbon, 2 parts by weight of Neopelex powder (trade name, produced by Kao K.K.) and 0.5 part by weight of Demol (trade name, produced by Kao K.K.) were uniformly mixed, and the mixture was then pulverized to obtain a wettable powder.

(3) Preparation of emulsifiable concentrate

Ten parts by weight of Toxanone (trade name, produced by Sanyo Kasei Kogyo) was added to 20 parts by weight of Compound 7 and 70 parts by weight of xylene, the mixture was uniformly mixed, and dissolved therein to obtain an emulsifiable concentrate.

(4) Preparation of dustable powder

Five parts by weight of Compound 7, 50 parts by weight of talc and 45 parts by weight of kaolin were uniformly mixed to obtain a dustable powder.

Example 3 (tests of effects)

(1) Test of controlling effect on cucumber downy mildew (preventive effect)

In plastic flowerpots having a diameter of 6 cm, one cucumber (variety: Sagami Hanshiro) was grown per one flowerpot, and to the young plants at 1.5 leaf stage, an acetone solution containing one kind of a compound among the desired compounds (1) shown in Table 3 obtained by diluting with water containing a surfactant (0.05%) to 200 or 40 ppm was sprayed in an amount of 20 ml per one flowerpot, respectively.

After spraying, the cucumbers were grown in a glass greenhouse for 2 days, and then, spores of cucumber downy mildew (*Pseudoperonospora cubensis*) were prepared from infected leaves and were sprayed uniformly to the back surface of plant leaves to be inoculated thereto.

After inoculation, the cucumbers were placed in a dark place at 20° C. for one day, and then, grown in a glass greenhouse for 5 days, and the degree of lesion of cucumber downy mildew appeared on the first leaves was examined.

Evaluation of the effects of the chemicals was carried out by measuring a controlling rate from the ratio of lesion surface area of the treated district based on that of the non-treated district, and the results are shown according to the 6 rank evaluation method described in Table 5.

TABLE 5

| Controlling value | |
|---|---|
| Preventive value | Controlling rate (%) |
| 5 | 100 |
| 4 | Less than 100 ~ 95 |
| 3 | Less than 95 ~ 81 |
| 2 | Less than 81 ~ 61 |
| 1 | Less than 61 ~ 31 |
| 0 | Less than 31 |

The results are shown in Table 6.

TABLE 6

| | Controlling value on cucumber downy mildew | | | | |
|---|---|---|---|---|---|
| | Spread concentration (ppm) | | | Spread concentration (ppm) | |
| Compound | 200 | 40 | Compound | 200 | 40 |
| 8 | 5 | — | 89 | 5 | — |
| 23 | 5 | — | 98 | 5 | — |
| 30 | 5 | — | 101 | 5 | — |
| 54 | 5 | — | 115 | 4 | — |
| 66 | 5 | 4 | 118 | 4 | 4 |
| 69 | 5 | — | 121 | 4 | — |
| 70 | 5 | — | 122 | 4 | — |
| 72 | 5 | — | 123 | 4 | 4 |
| 74 | 5 | 4 | 126 | 4 | — |
| 87 | 5 | — | 141 | 5 | 4 |

(2) Test of controlling effect on cucumber gray mold (Paper disc test)

Paper moisturized by water was spread all over in an apparatus and seed leaves of cucumber (variety: Sagami Hanshiro) was placed thereon, then, a suspension of lesion of cucumber gray mold was dropped on the seed leaves in an amount of 50 μl, and a paper disc was further placed thereon.

An acetone solution containing one kind of a compound amount the desired compounds (1) shown in Table 3 obtained by diluting with water containing a surfactant (0.05%) to 500 ppm was immediately dropped on the paper disc in an amount of 90 μl.

Thereafter, the leaves were placed in a dark place at 20° C. for 4 days, and then, the degree of lesion of cucumber gray mold appeared on the seed leaves was examined.

Evaluation of the effects of the chemicals was shown in the following Table 7 with the same 6-ranks of controlling value obtained by the same manner as in the above-mentioned (1).

TABLE 7

Controlling value on cucumber gray mold

| Compound | Spread concentration (ppm) 500 |
|---|---|
| 10 | 4 |
| 20 | 4 |
| 33 | 5 |

(3) Test of controlling effect on rice blast (preventive effect)

In plastic flowerpots having a diameter of 6 cm, 10 rice seedlings (variety: Nihonbare) were grown per one flowerpot, and to the young plants at 2.5 leaf stage, an acetone solution containing one kind of a compound among the desired compounds (1) shown in Table 3 obtained by diluting with water containing a surfactant (0.05%) to 200 or 40 ppm was sprayed in an amount of 20 ml per one flowerpot, respectively.

After spraying, the rice seedlings were grown in a glass greenhouse for 2 days, and then a suspension of conidiospores of rice blast (*Pyricularia oryzae*) prepared from infected leaves was sprayed uniformly to the plant leaves to be inoculated thereto.

After inoculation, the rice seedlings were grown in a moist chamber at 28° C. for 5 days, and the degree of lesion of rice blast appeared on the leaves was examined.

Evaluation of the effects of the chemicals was shown in the following Table 8 with the 6 rank controlling values obtained by the same manner as in the above-mentioned (1).

TABLE 8

Controlling value on rice blast

| Com-pound | Spread concentration (ppm) | | Com-pound | Spread concentration (ppm) | |
|---|---|---|---|---|---|
| | 200 | 40 | | 200 | 40 |
| 2 | 5 | 4 | 82 | 5 | 4 |
| 8 | 5 | — | 86 | 5 | — |
| 23 | 5 | 5 | 87 | 5 | — |
| 25 | 5 | 5 | 89 | 5 | 5 |
| 27 | 5 | 5 | 90 | 5 | 4 |
| 30 | 5 | 4 | 91 | 5 | — |
| 33 | 5 | — | 96 | 5 | — |
| 38 | 5 | — | 98 | 5 | 4 |
| 45 | 5 | 5 | 88 | 5 | 5 |
| 60 | 5 | — | 103 | 5 | 4 |
| 64 | 5 | — | 105 | 5 | 4 |
| 66 | 5 | 4 | 114 | 5 | — |
| 68 | 5 | 4 | 115 | 5 | 4 |
| 72 | 5 | 4 | 123 | 5 | 5 |
| 74 | 5 | 4 | 144 | 5 | 4 |
| 75 | 5 | 4 | | | |

(4) Test of controlling effect on barley powdery mildew (preventive effect)

In plastic flowerpots having a diameter of 6 cm, 10 barley seedlings (variety: Kuromugi) were grown per one flowerpot, and to the young plants at 1.5 leaf stage, an acetone solution containing one kind of a compound among the desired compounds (1) shown in Table 3 was diluted with water containing a surfactant (0.05%) to 200 or 40 ppm and these respective solutions were sprayed in an amount of 20 ml per one flowerpot, respectively.

After spraying, the barley seedlings were grown in a glass greenhouse for 2 days, and then, spores of barley powdery mildew (*Erysiphe graminis*) were collected from infected leaves and were sprayed uniformly on the plants to be inoculated thereto.

Next, the barley seedlings were grown in a glass greenhouse for 10 days, and the degree of lesion of barley powdery mildew appeared on the respective first leaves was examined.

Evaluation of the effects of the chemicals was shown in the following Table 8 with the 6 rank controlling values obtained by the same manner as in the above-mentioned (1).

TABLE 9

Controlling value on barley powdery mildew

| Com-pound | Spread concentration (ppm) | | Com-pound | Spread concentration (ppm) | |
|---|---|---|---|---|---|
| | 200 | 40 | | 200 | 40 |
| 23 | 5 | 5 | 101 | 5 | — |
| 27 | 5 | — | 102 | 5 | 4 |
| 30 | 5 | — | 103 | 5 | 5 |
| 33 | 5 | — | 103 | 5 | — |
| 45 | 5 | — | 105 | 5 | 4 |
| 46 | 5 | — | 108 | 5 | 4 |
| 54 | 5 | — | 109 | 5 | 4 |
| 61 | 5 | — | 111 | 5 | — |
| 62 | 5 | 5 | 113 | 5 | 4 |
| 64 | 5 | — | 114 | 5 | 5 |
| 66 | 5 | 4 | 115 | 5 | — |
| 68 | 5 | 4 | 116 | 5 | 5 |
| 69 | 5 | 4 | 117 | 5 | 5 |
| 72 | 5 | — | 119 | 5 | 4 |
| 74 | 5 | — | 120 | 5 | 4 |
| 82 | 5 | 4 | 122 | 5 | 4 |
| 87 | 5 | 4 | 123 | 5 | 5 |
| 89 | 5 | — | 124 | 5 | — |
| 96 | 5 | 4 | 126 | 5 | — |
| 99 | 5 | — | 135 | 5 | 4 |

(5) Test of controlling effect on cucumber powdery mildew preventive effect)

In plastic flowerpots having a diameter of 6 cm, one cucumber (variety: Sagami Hanshiro) was grown per one flowerpot, and to the young plants at 1 to 1.5 leaf stage, an acetone solution containing one kind of a compound among the desired compounds (1) shown in Table 3 prepared by diluting with water containing a surfactant (0.05%) to 100 or 50 ppm was sprayed in an amount of 10 ml per one flowerpot, respectively.

After spraying, the cucumbers were grown in a glass greenhouse for 2 days, and then, a suspension of conidiospores of cucumber powdery mildew were sprayed uniformly on the plant leaves to be inoculated thereto.

After inoculation, the cucumbers were grown in a glass greenhouse for 10 days, and the degree of lesion of cucumber powdery mildew appeared on the respective first leaves was examined.

Evaluation of the effects of the chemicals was shown in the following Table 10 with the 6 rank controlling value obtained by the same manner as in the above-mentioned (1).

TABLE 10

Controlling value on cucumber powdery mildew

| Compound | Spread concentration (ppm) | |
|---|---|---|
| | 100 | 50 |
| 23 | 5 | 4 |
| 68 | 5 | 4 |

(6) Test of controlling effect on wheat brown rust (preventive effect)

In plastic flowerpots having a diameter of 6 cm, 10 wheat seedlings (variety: Kobushi Komugi) were grown per one flowerpot, and to the young plants at 1.5 leaf stage, an acetone solution containing one kind of a compound among the desired compounds (1) shown in Table 3 was diluted with water containing a surfactant (0.05%) to 200 or 40 ppm and these respective solutions were sprayed in an amount of 20 ml per one flowerpot, respectively.

After spraying, the wheat seedlings were grown in a glass greenhouse for 2 days, and then a suspension of spores of wheat brown rust (*Puccinia recondiat*) was sprayed uniformly to the plants to be inoculated thereto.

After inoculation, the wheat seedlings were grown in a glass greenhouse for 10 days, and the degree of lesion of wheat brown rust appeared on the first leaves was examined.

Evaluation of the effects of the chemicals was shown in the following Table 11 with the 6 rank controlling values obtained by the same manner as in the above-mentioned (1).

TABLE 11

Controlling value on wheat brown rust

| Compound | Spread concentration (ppm) | | Compound | Spread concentration (ppm) | |
|---|---|---|---|---|---|
| | 200 | 40 | | 200 | 40 |
| 23 | 5 | 5 | 102 | 5 | — |
| 27 | 5 | — | 103 | 5 | 5 |
| 30 | 5 | 4 | 104 | 5 | 4 |
| 33 | 5 | 4 | 105 | 5 | 4 |
| 45 | 5 | 4 | 114 | 5 | — |
| 54 | 5 | — | 115 | 4 | 4 |
| 62 | 5 | 4 | 116 | 5 | 5 |
| 64 | 5 | — | 117 | 5 | 4 |
| 66 | 5 | — | 118 | 4 | — |
| 68 | 5 | 4 | 120 | 4 | 4 |
| 69 | 5 | 4 | 121 | 4 | — |
| 74 | 5 | — | 123 | 5 | 5 |
| 89 | 5 | 4 | 126 | 5 | 4 |
| 90 | 5 | 4 | 127 | 5 | 4 |
| 98 | 5 | 4 | | | |

(7) Antifungal test on rice sheath blight

In plastic flowerpots having a diameter of 6 cm, a rice seedling (variety: Nihonbare) was grown per one flowerpot, and to the young plants at 2.5 to 3.5 leaf stage, an acetone solution containing one kind of a compound among the desired compounds (1) shown in Table 3 obtained by diluting with water containing a surfactant (0.05%) to 100 or 25 ppm was sprayed in an amount of 30 ml per one flowerpot, respectively.

24 hours after spraying, an inoculating source (a bran medium in which rice sheath blight was cultured was diluted with 50 ml of water and increased to 10-fold by dried rice husks) was spread all over the roots of rice seedlings.

After inoculation, the rice seedlings were grown in a moist chamber at 28° C. for 7 days, and growths of rice sheath blight and rice plants were examined.

Evaluation of the effects of the chemicals was shown in the following Table 13 with the controlling values shown with the standard A to D in Table 12.

TABLE 12

| Controlling value | Controlling value | |
|---|---|---|
| | Increase of hyphae and growing conditions of rice | |
| A | *No increase in hyphae was observed. | |
| | *Increase in hyphae was observed. | |
| B | *There is no bad effect on growth of rice. | |
| | *Increase in hyphae was observed. | |
| C | *There is bad effect on growth of rice. | |
| D | *Rice dead. | |

TABLE 13

Controlling value on rice sheath blight

| Compound | Spread concentration (ppm) | |
|---|---|---|
| | 100 | 25 |
| 17 | A | B |
| 23 | A | B |
| 74 | A | B |

Utilizability in industry

The novel N-phenyl carbamate compound of the present invention has excellent fungicidal effect for agricultural and horticultural use.

We claim:

1. An N-phenyl carbamate compound which is represented by the following formula (1):

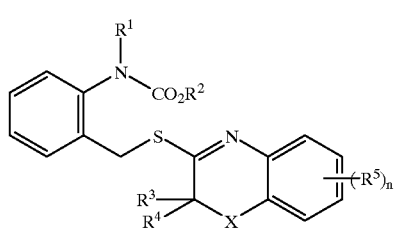

(1)

wherein $R^1$ represents a hydrogen atom, an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ or an alkoxy group having 1 to 4 carbon atoms;

where, R represents an alkyl group having 1 to 4 carbon atoms;

$R^2$ represents an alkyl group having 1 to 4 carbon atoms;

$R^3$ and $R^4$ each independently represent a hydrogen atom or an alkyl group having 1 to 4 carbon atoms;

$R^5$ represents a hydrogen atom, an alkyl group having 1 to 8 carbon atoms, a haloalkyl group having 1 to 4 carbon atoms, a halogen atom, an alkylcarbonyl group having 2 to 5 carbon atoms, a phenyl group, an alkoxycarbonyl group having 2 to 5 carbon atoms, an alkylsulfonyl group having 1 to 4 carbon atoms, a nitro group, a cyano group, a benzyloxycarbonyl group or a haloalkoxy group having 1 to 4 carbon atoms;

X represents O or S; and n represents 1, 2 or 3.

2. The N-phenyl carbamate compound according to claim 1, wherein $R^1$ is a hydrogen atom, $CH_2OCH_3$, $CH_2OC_2H_5$, $CH_3$, $C_2H_5$, n-$C_3H_7$, $CH_2CH=CH_2$, $CO_2CH_3$, $OCH_3$ or $OC_2H_5$.

3. The N-phenyl carbamate compound according to claim 1, wherein $R^2$ is $CH_3$ or $C_2H_5$.

4. The N-phenyl carbamate compound according to claim 1, wherein $R^3$ and $R^4$ are each a hydrogen atom, $CH_3$ or $C_2H_5$.

5. The N-phenyl carbamate compound according to claim 1, wherein $R^5$ is a hydrogen atom, $CH_3$, $C_2H_5$, n-$C_3H_7$, n-$C_4H_9$, t-$C_4H_9$, n-$C_5H_{11}$, a trifluoromethyl group, a chlorine atom, a bromine atom, a fluorine atom, an ethylcarbonyl group, a phenyl group, a propoxycarbonyl group, an ethylsulfonyl group, a nitro group, a cyano group, a benzyloxycarbonyl group or a trifluoromethoxy group.

6. The N-phenyl carbamate compound according to claim 1, wherein $R^1$ is a hydrogen atom and the compound is represented by the following formula (1-a):

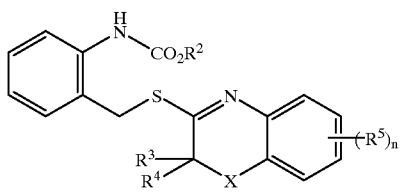

(1-a)

wherein $R^2$ to $R^5$, X and n have the same meanings as defined in claim 1.

7. The N-phenyl carbamate compound according to claim 1, wherein $R^1$ is $R^{1'}$ and the compound is represented by the following formula (1-b):

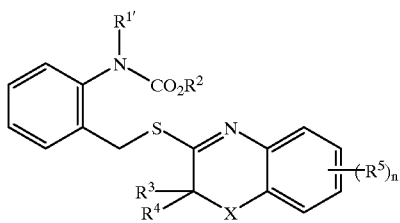

(1-b)

wherein $R^{1'}$, represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms or $CO_2R^6$, where $R^2$ to $R^6$, X and n have the same meanings as defined in claim 1.

8. The N-phenyl carbamate compound according to claim 1, wherein $R^1$ is $R^{1''}$ and the compound is represented by the following formula (1-c):

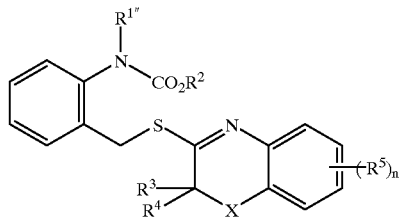

(1-c)

wherein $R^{1''}$ represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ or an alkoxy group having 1 to 4 carbon atoms, where $R^2$ to $R^6$, X and n have the same meanings as defined in claim 1.

9. The N-phenyl carbamate compound according to claim 1, wherein said compound is selected from the group consisting of:

(1) A compound in which $R^1$ is an alkoxyalkyl group having 2 to 5 carbon atoms, $R^2$ is an alkyl group having 2 to 5 carbon atoms, $R^3$ and $R^4$ are both hydrogen atoms, X is an oxygen atom, and $(R^5)_n$ is a hydrogen atom;

(2) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is a sulfur atom, and $(R^5)_n$ is a hydrogen atom;

(3) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkyl group having 1 to 4 carbon atoms at the substitution position of 5-, 6- or 7-position;

(4) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a haloalkyl group having 1 to 4 carbon atoms at the substitution position of 6- or 8-position;

(5) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a haloalkyl group having 1 to 4 carbon atoms at the substitution position of 6- or 8-position;

(6) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a halogen atom at the substitution position of 6-position;

(7) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a halogen atom at the substitution position of 6-position;

(8) A compound in which $R^1$ is an alkoxyalkyl group having 2 to 5 carbon atoms, $R^2$ and $R^3$ are alkyl groups having 1 to 4 carbon atoms, $R^4$ is a hydrogen atom, X is an oxygen atom, n in $(R^5)_n$ is 1 and $R^5$ is a halogen atom at the substitution position of 6-position;

(9) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkyl group having 1 to 4 carbon atoms at the substitution position of 5-, 6- or 7-position;

(10) A compound in which $R^1$, $R^3$ and $R^4$ are all hydrogen atoms, $R^2$ is an alkyl group having 1 to 4 carbon atoms, X is an oxygen atom, n in $(R^5)_n$ is 2 and $R^5$'s are an alkyl group having 1 to 4 carbon atoms at the substitution position of 6-, 7- or 8-position or a halogen atom at the substitution position of 6- or 8-position;

(11) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are an alkyl group having 1 to 4 carbon atoms at the substitution position of 6-, 7- or 8-position and a halogen atom at the substitution position of 6- or 8-position;

(12) A compound in which $R^1$ is an alkynyl group having 2 to 5 carbon atoms, $R^2$ is an alkyl group having 1 to 4 carbon atoms, $R^3$ and R, are both hydrogen atoms, X is an oxygen atom, n in $(R^5)_n$ is 2 and $R^5$'s are an alkyl group having 1 to 4 carbon atoms at the substitution position of 6-, 7- or 8-position and a halogen atom at the substitution position of 6- or 8-position;

(13) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are a haloalkyl group having 1 to 4 carbon atoms at the substitution position of 6-position and a halogen atom at the substitution position of 8-position;

(14) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are a haloalkyl group having 1 to 4 carbon atoms at the substitution position of 6-position and a halogen atom at the substitution position of 8-position;

(15) A compound in which $R^1$, $R^3$ and $R^4$ are all hydrogen atoms, $R^2$ is an alkyl group having 1 to 4 carbon atoms, X is an oxygen atom, n in $(R^5)_n$ is 2 and $R^5$'s are halogen atoms at the substitution positions of 6-, 7- or 8-position;

(16) A compound in which $R^1$ is an alkoxyalkyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are halogen atoms at the substitution positions of 6-, 7- or 8-position;

(17) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are halogen atoms at the substitution positions of 6-, 7- or 8-position;

(18) A compound in which $R^1$ and $R^2$ are both alkyl groups having 1 to 4 carbon atoms, $R^3$ and $R^4$ are both hydrogen atoms, X is an oxygen atom, n in $(R^5)_n$ is 2 and $R^5$'s are an alkyl group having 1 to 4 carbon atoms at the substitution position of 6-, 7- or 8-position and a halogen atom at the substitution position of 6- or 8-position;

(19) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkyl group having 1 to 4 carbon atoms at the substitution position of 5-, 6- or 7-position;

(20) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a haloalkyl group having 1 to 4 carbon atoms at the substitution position of 6- or 8-position;

(21) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a halogen atom at the substitution position of 6-position;

(22) A compound in which $R^1$ is an alkoxy group having 1 to 4 carbon atoms, $R^2$ is an alkyl group having 1 to 4 carbon atoms, $R^3$ is an alkyl group having 1 to 4 carbon atoms, $R^4$ is a hydrogen atom, X is an oxygen atom, n in $(R^5)_n$ is 1 and $R^5$ is a halogen atom at the substitution position of 6-position;

(23) A compound in which $R^1$ is an alkoxy group having 1 to 4 carbon atoms, $R^2$ to $R^4$ are alkyl groups having 1 to 4 carbon atoms, X is an oxygen atom, n in $(R^5)_n$ is 1 and $R^5$ is a halogen atom at the substitution position of 8-position;

(24) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are halogen atom at the substitution position of 5- or 8-position and $NO_2$ at the substitution position of 7-position;

(25) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are an alkyl group having 1 to 4 carbon atoms at the substitution position of 6-, 7- or 8-position and a halogen atom at the substitution position of 6- or 8-position;

(26) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are a haloalkyl group having 1 to 4 carbon atoms at the substitution position of 6-position and a halogen atom at the substitution position of 8-position;

(27) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is a phenyl group;

(28) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkylcarbonyl group having 1 to 4 carbon atoms;

(29) A compound in which $R^1$ is an alkoxy group having 1 to 4 carbon atoms, $R^2$ to $R^4$ are alkyl groups each having 1 to 4 carbon atoms, X is an oxygen atom, n in $(R^5)_n$ is 2 and $R^5$'s are a haloalkyl group having 1 to 4 carbon atoms at the substitution position of 6-position and a halogen atom at the substitution position of 8-position;

(30) A compound in which $R^1$ is an alkoxy group having 1 to 4 carbon atoms, $R^2$ is an alkyl group having 1 to

43

4 carbon atoms, $R^3$ and $R^4$ are both hydrogen atoms, X is an oxygen atom, n in $(R^5)_n$ is 1 and $R^5$ is an alkylsulfonyl group having 1 to 4 carbon atoms;

(31) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkoxycarbonyl group having 2 to 5 carbon atoms;

(32) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are a haloalkoxy group having 1 to 4 carbon atoms at the substitution position of 6-position and a halogen atom at the substitution position of 8-position;

(33) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are a haloalkoxy group having 1 to 4 carbon atoms at the substitution position of 6-position and a halogen atom at the substitution position of 8-position;

(34) A compound in which $R^1$ is an alkoxy group having 1 to 4 carbon atoms, $R^2$ is an alkyl group having 1 to 4 carbon atoms, $R^3$ and $R^4$ are both hydrogen atoms, X is an oxygen atom, n in $(R^5)_n$ is 1 and $R^5$ is an alkyl group having 1 to 8 carbon atoms at the substitution position of 5-, 6- or 7-position;

(35) A compound in which $R^1$ is an alkynyl group having 2 to 5 carbon atoms, $R^2$ is an alkyl group having 1 to 4 carbon atoms, $R^3$ and $R^4$ are both hydrogen atoms, X is an oxygen atom, n in $(R^5)_n$ is 2 and $R^5$'s are an alkylcarbonyl group having 2 to 5 carbon atoms at the substitution position of 6- or 8-position and a halogen atom at the substitution position of 5-, 6- or 7-positoin; and

(36) A compound in which $R^1$ and $R^2$ are both alkyl groups having 1 to 4 carbon atoms, $R^3$ and $R^4$ are both hydrogen atoms, X is an oxygen atom, n in $(R^5)_n$ is 1 and $R^5$ is a halogen atom at the substitution position of 6- or 8-position.

10. The N-phenyl carbamate compound according to claim 1, wherein said compound is selected from the group consisting of:

(1) Methyl N-[2-(2H-1,4-benzoxazin-3-ylthiomethyl) phenyl]-carbamate (Compound 1)

(2) Methyl N-(methoxymethyl)-N-[2-(2H-1,4-benzothiazin-3-ylthiomethyl)phenyl]carbamate (Compound 8)

(3) Methyl N-(methoxymethyl)-N-[2-(6-methyl-2H-1,4-benzoxazin-3-ylthiomethyl)phenyl]carbamate (Compound 10)

(4) Methyl N-[2-[(6-trifluoromethyl-2H-1,4-benzoxazin-3-ylthio)methyl]phenyl]carbamate (Compound 22)

(5) Methyl N-(methoxymethyl)-N-[2-[(6-trifluoromethyl-2H-1,4-benzoxazin-3-ylthio)methyl]phenyl]carbamate (Compound 23)

(6) Methyl N-(propargyl)-N-[2-[(6-trifluoromethyl-2H-1, 4-benzoxazin-3-ylthio)methyl]phenyl]carbamate (Compound 25)

(7) Methyl N-(methoxymethyl)-N-[2-(6-fluoro-2H-1,4-benzoxazin-3-ylthiomethyl)phenyl]carbamate (Compound 27)

(8) Methyl N-(propargyl)-N-[2-[(6-chloro-2H-1,4-benzoxazin-3-ylthio)methyl]phenyl]carbamate (Compound 33)

44

(9) Methyl N-(methoxymethyl)-N-[2-(6-chloro-2-methyl-2H-1,4-benzoxazin-3-ylthiomethyl)phenyl]carbamate (Compound 38)

(10) Methyl N-(propargyl)-N-[2-(7-methyl-2H-1,4-benzoxazin-3-ylthiomethyl)phenyl]carbamate (Compound 54)

(11) Methyl N-[2-(6-chloro-7-ethyl-2H-1,4-benzoxazin-3-ylthiomethyl)phenyl]carbamate (Compound 60)

(12) Methyl N-(methoxymethyl)-N-[2-(6-chloro-7-ethyl-2H-1,4-benzoxazin-3-ylthiomethyl)phenyl]carbamate (Compound 61)

(13) Methyl N-(propargyl)-N-[2-(6-chloro-7-ethyl-2H-1, 4-benzoxazin-3-ylthiomethyl)phenyl]carbamate (Compound 62)

(14) Methyl N-[2-[(8-chloro-6-trifluoromethyl-2H-1,4-benzoxazin-3-ylthio)methyl]phenyl]carbamate (Compound 67)

(15) Methyl N-(methoxymethyl)-N-[2-[(8-chloro-6-trifluoromethyl-2H-1,4-benzoxazin-3-ylthio)methyl] phenyl]-carbamate (Compound 68)

(16) Methyl N-(propargyl)-N-[2-[(8-chloro-6-trifluoromethyl-2H-1,4-benzoxazin-3-ylthio)methyl] phenyl]carbamate (Compound 69)

(17) Methyl N-[2-(6,8-difluoro-2H-1,4-benzoxazin-3-ylthiomethyl)phenyl]carbamate (Compound 70)

(18) Methyl N-[2-(6,8-dichloro-2H-1,4-benzoxazin-3-ylthiomethyl)phenyl]carbamate (Compound 73)

(19) Methyl N-(methoxymethyl)-N-[2-[(6,8-dichloro-2H-1,4-benzoxazin-3-ylthiomethyl)phenyl]carbamate (Compound 74)

(20) Methyl N-(propargyl)-N-[2-(6,8-dichloro-2H-1,4-benzoxazin-3-ylthiomethyl)phenyl]carbamate (Compound 75)

(21) Methyl N-(ethyl)-N-[2-(6-ethyl-8-chloro-2H-1,4-benzoxazin-3-ylthiomethyl)phenyl]carbamate (Compound 82)

(22) Methyl N-(methoxy)-N-[2-(6-tert-butyl-2H-1,4-benzoxazin-3-ylthiomethyl)phenyl]carbamate (Compound 86)

(23) Methyl N-(methoxy)-N-[2-(6-trifluoromethyl-2H-1, 4-benzoxazin-3-ylthiomethyl)phenyl]carbamate (Compound 87)

(24) Methyl N-[2-[(6-chloro-2H-1,4-benzoxazin-3-ylthio)methyl]phenyl]-N-methoxy carbamate (Compound 89)

(25) Methyl N-[2-[(6-chloro-2-methyl-2H-1,4-benzoxazin-3-ylthio)methyl]phenyl]-N-methoxy carbamate (Compound 90)

(26) Methyl N-(methoxy)-N-[2-(2,2-dimethyl-6-chloro-2H-1,4-benzoxazin-3-ylthiomethyl)phenyl]carbamate (Compound 91)

(27) Methyl N-[2-[(8-chloro-6-trifluoromethyl-2H-1,4-benzoxazin-3-ylthio)methyl]phenyl]-N-methoxy carbamate (Compound 103)

(28) Methyl N-[2-[(6-chloro-8-methyl-2H-1,4-benzoxazin-3-ylthio)methyl]phenyl]-N-methoxy carbamate (Compound 104)

(29) Methyl N-[2-[(6,8-dichloro-2H-1,4-benzoxazin-3-ylthio)methyl]phenyl]-N-methoxy carbamate (Compound 105)

(30) Methyl N-(propargyl)-N-[2-(6-phenyl-2H-1,4-benzoxazin-3-ylthiomethyl)phenyl]carbamate (Compound 115)

(31) Methyl N-(methoxy)-N-[2-(6-propionyl-8-chloro-2H-1,4-benzoxazin-3-ylthiomethyl)phenyl]carbamate (Compound 118)

(32) Methyl N-(methoxy)-N-[2-(5-trifluoromethyl-6-fluoro-2H-1,4-benzoxazin-3-ylthiomethyl)phenyl] carbamate (Compound 119)

(33) Methyl N-(methoxy)-N-[2-(6-ethanesulfonyl-2H-1,4-benzoxazin-3-ylthiomethyl)phenyl]carbamate (Compound 121)

(34) Methyl N-(methoxy)-N-[2-[6-(prop-2-yloxycarbonyl)-2H-1,4-benzoxazin-3-ylthiomethyl] phenyl]carbamate (Compound 122)

(35) Methyl N-(methoxy)-N-[2-(6-trifluoromethoxy-8-chloro-2H-1,4-benzoxazin-3-ylthiomethyl)phenyl] carbamate (Compound 123)

(36) Methyl N-(propargyl)-N-[2-(6-trifluoromethoxy-8-chloro-2H-1,4-benzoxazin-3-ylthiomethyl)phenyl] carbamate (Compound 124)

(37) Methyl N-(methoxy)-N-[2-(6-n-butyl-2H-1,4-benzoxazin-3-ylthiomethyl)phenyl]carbamate (Compound 135)

(38) Methyl N-(propargyl)-N-[2-(6-propionyl-8-chloro-2H-1,4-benzoxazin-3-ylthiomethyl)phenyl]carbamate (Compound 141) and

(39) Methyl N-(methyl)-N-[2-(6-chloro-2H-1,4-benzoxazin-3-ylthiomethyl)phenyl]carbamate (Compound 144).

11. A process for producing an N-phenyl carbamate compound represented by the following formula (1-a) in claim 6 which comprises reacting a compound represented by the following formula (2):

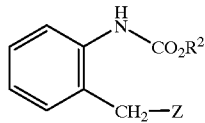

(2)

wherein $R^2$ has the same meaning as defined in claim 6, and Z is a chlorine atom or a bromine atom, and a compound represented by the following formula (3):

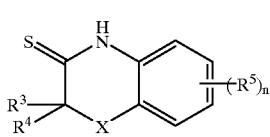

(3)

wherein $R^3$ to $R^5$, X and n have the same meanings as defined above.

12. A process for producing an N-phenyl carbamate compound represented by the formula (1-b) in claim 7 which comprises reacting the compound represented by the following formula (1-a):

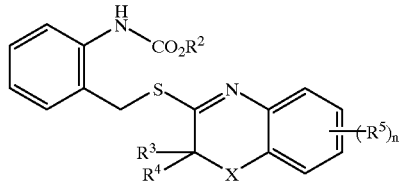

(1-a)

wherein $R^2$ to $R^5$, X and n have the same meanings as defined in claim 7, with a compound represented by the following formula (4):

(4)

wherein $R^{1'}$ represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms or $CO_2R^6$, where $R^6$ represents an alkyl group having 1 to 4 carbon atoms;

and W represents a chlorine atom, a bromine atom or an iodine atom.

13. A process for producing an N-phenyl carbamate compound represented by the following formula (1-c) in claim 8 which comprises reacting a compound represented by the following formula (5):

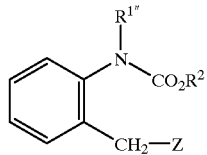

(5)

wherein $R^{1''}$ represents an alkoxyalkyl group having 2 to 5 carbon atoms, an alkynyl group having 2 to 5 carbon atoms, an alkyl group having 1 to 4 carbon atoms, an alkenyl group having 2 to 5 carbon atoms, $CO_2R^6$ or an alkoxy group having 1 to 4 carbon atoms, where $R^6$ represents an alkyl group having 1 to 4 carbon atoms; and $R^2$ and Z have the same meanings as defined in claim 8, and a compound represented by the following formula (3):

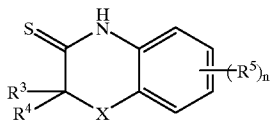

(3)

wherein $R^3$ to $R^5$, X and n have the same meanings as defined in claim 8.

14. An agricultural or horticultural fungicide which comprises the N-phenyl carbamate represented by the formula (1) according to claim 1 as an effective ingredient and an agriculturally or horticulturally acceptable carrier.

* * * * *